US011986163B2

(12) United States Patent
Onobori et al.

(10) Patent No.: US 11,986,163 B2
(45) Date of Patent: May 21, 2024

(54) ENDOSCOPE AND ENDOSCOPE SYSTEM CONTROLLED BY PAIR OF CABLE BUNDLES

(71) Applicant: HOYA CORPORATION, Tokyo (JP)

(72) Inventors: Kunihiko Onobori, Tokyo (JP); Kohei Iketani, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 400 days.

(21) Appl. No.: 17/257,358

(22) PCT Filed: Dec. 24, 2019

(86) PCT No.: PCT/JP2019/050640
§ 371 (c)(1),
(2) Date: Dec. 31, 2020

(87) PCT Pub. No.: WO2020/138091
PCT Pub. Date: Jul. 2, 2020

(65) Prior Publication Data
US 2021/0267439 A1    Sep. 2, 2021

(30) Foreign Application Priority Data

Dec. 28, 2018   (JP) ................................ 2018-248160

(51) Int. Cl.
*A61B 1/06* (2006.01)
*A61B 1/00* (2006.01)
(Continued)

(52) U.S. Cl.
CPC ............ *A61B 1/06* (2013.01); *A61B 1/00121* (2013.01); *A61B 1/00167* (2013.01);
(Continued)

(58) Field of Classification Search
CPC ..... A61B 1/00167; A61B 1/0051; A61B 1/05; A61B 1/07; A61B 1/00121; A61B 1/053; A61B 1/00128; A61B 1/0057
(Continued)

(56) References Cited

U.S. PATENT DOCUMENTS 4,991,957 A * 2/1991 Sakamoto ............... A61B 1/009
356/241.4
5,083,223 A * 1/1992 Igarashi ............... G02B 23/243
359/708
(Continued)

FOREIGN PATENT DOCUMENTS

CN        107920716 A     4/2018
DE   10 2016 216 380 A1   2/2017
(Continued)

OTHER PUBLICATIONS

Office Action issued in Chinese Counterpart Patent Appl. No. 201980045624.6, dated Jan. 19, 2022.
(Continued)

*Primary Examiner* — John P Leubecker
*Assistant Examiner* — Li-Ting Song
(74) *Attorney, Agent, or Firm* — GREENBLUM & BERNSTEIN, P.L.C.

(57) ABSTRACT

An endoscope includes an insertion portion that is covered with an exterior tube with an outer diameter of 1 mm or less, an observation optical system that includes a rectangular image sensor fixed to a tip of the insertion portion and having a length of one side of 60% or less of the outer diameter of the insertion portion, an illumination fiber that is arranged between an inner surface of the exterior tube and an edge of the observation optical system and penetrates the exterior tube, a cable bundle that is connected to the image
(Continued)

sensor and penetrates the exterior tube, and a connector that is connected to the cable bundle and the illumination fiber.

13 Claims, 27 Drawing Sheets

(51) Int. Cl.
    *A61B 1/005* (2006.01)
    *A61B 1/04* (2006.01)
    *A61B 1/05* (2006.01)
    *A61B 1/07* (2006.01)
(52) U.S. Cl.
    CPC ............ *A61B 1/005* (2013.01); *A61B 1/0051* (2013.01); *A61B 1/04* (2013.01); *A61B 1/05* (2013.01); *A61B 1/07* (2013.01)
(58) Field of Classification Search
    USPC ......................................................... 600/132
    See application file for complete search history.

(56) References Cited

U.S. PATENT DOCUMENTS

| | | | | |
|---|---|---|---|---|
| 5,188,094 | A * | 2/1993 | Adair | A61B 1/05 600/122 |
| 5,704,892 | A * | 1/1998 | Adair | A61B 1/015 600/125 |
| 10,813,537 | B2 | 10/2020 | Kuboi | |
| 2003/0222325 | A1* | 12/2003 | Jacobsen | A61B 1/05 257/434 |
| 2005/0228452 | A1* | 10/2005 | Mourlas | A61M 25/1002 606/41 |
| 2007/0015964 | A1* | 1/2007 | Eversull | A61B 1/05 600/114 |
| 2010/0280525 | A1* | 11/2010 | Alvarez | A61B 1/0055 606/130 |
| 2013/0109919 | A1* | 5/2013 | Sugiyama | A61B 1/00006 600/117 |
| 2013/0197309 | A1* | 8/2013 | Sakata | A61B 1/00128 600/132 |
| 2015/0088152 | A1 | 3/2015 | Hatta | |
| 2017/0042573 | A1* | 2/2017 | Savvouras | A61B 17/3474 |
| 2017/0059848 | A1 | 3/2017 | Haraguchi et al. | |
| 2017/0127915 | A1* | 5/2017 | Viebach | A61B 1/0057 |
| 2017/0245890 | A1* | 8/2017 | Ochi | A61B 1/0684 |
| 2017/0307872 | A1* | 10/2017 | Hatase | H04N 23/51 |
| 2018/0160882 | A1 | 6/2018 | Kuboi | |

FOREIGN PATENT DOCUMENTS

| | | |
|---|---|---|
| JP | 2000-028929 | 1/2000 |
| JP | 2001-137180 | 5/2001 |
| JP | 2008-212309 | 9/2008 |
| JP | 2011-019792 | 2/2011 |
| JP | 2012-090970 | 5/2012 |
| JP | 2015-062533 | 4/2015 |
| JP | 2016-116807 | 6/2016 |
| JP | 2017-185024 | 10/2017 |
| JP | 2017-195965 | 11/2017 |

OTHER PUBLICATIONS

Official Communication issued in International Bureau of WIPO Patent Application No. PCT/JP2019/050640, dated Mar. 17, 2020.
Office Action issued in German Patent Appl. No. 112019006478.9, dated Mar. 2, 2023, together wth an English translation.
Office Action issued in German Patent Appl. No. 112019006478.9, dated Jul. 4, 2023, together wth an English translation.

* cited by examiner

ENDOSCOPE AND ENDOSCOPE SYSTEM CONTROLLED BY PAIR OF CABLE BUNDLES

TECHNICAL FIELD

The present invention relates to an endoscope and an endoscope system.

BACKGROUND ART

An endoscope capable of observing the inner surface of an organ such as the digestive tract is used (Patent Literature 1). Specifications such as the thickness, length, and image quality of the endoscope are determined according to the characteristics of the observation target site. An endoscope with a diameter of about 3 mm, which is suitable for endoscopic examination of children, has been proposed (Patent Literature 2).

CITATION LIST

Patent Literature

Patent Literature 1: JP 2011-19792 A
Patent Literature 2: JP 2008-212309 A

SUMMARY OF INVENTION

Technical Problem

There are areas that cannot be reached even with an endoscope with a diameter of 3 mm, such as the peripheral part of the pancreatic bile duct and the area after the third branch of the bronchus. According to an aspect, an object is to provide a smaller diameter endoscope.

Solution to Problem

An endoscope includes an insertion portion that is covered with an exterior tube with an outer diameter of 1 mm or less, an observation optical system that includes a rectangular image sensor fixed to a tip of the insertion portion and having a length of one side of 60% or less of the outer diameter of the insertion portion, an illumination fiber that is arranged between an inner surface of the exterior tube and an edge of the observation optical system and penetrates the exterior tube, a cable bundle that is connected to the image sensor and penetrates the exterior tube, and a connector that is connected to the cable bundle and the illumination fiber.

Advantageous Effects of Invention

According to an aspect, a small diameter endoscope can be provided.

DESCRIPTION OF EMBODIMENTS

First Embodiment

Figure 1:
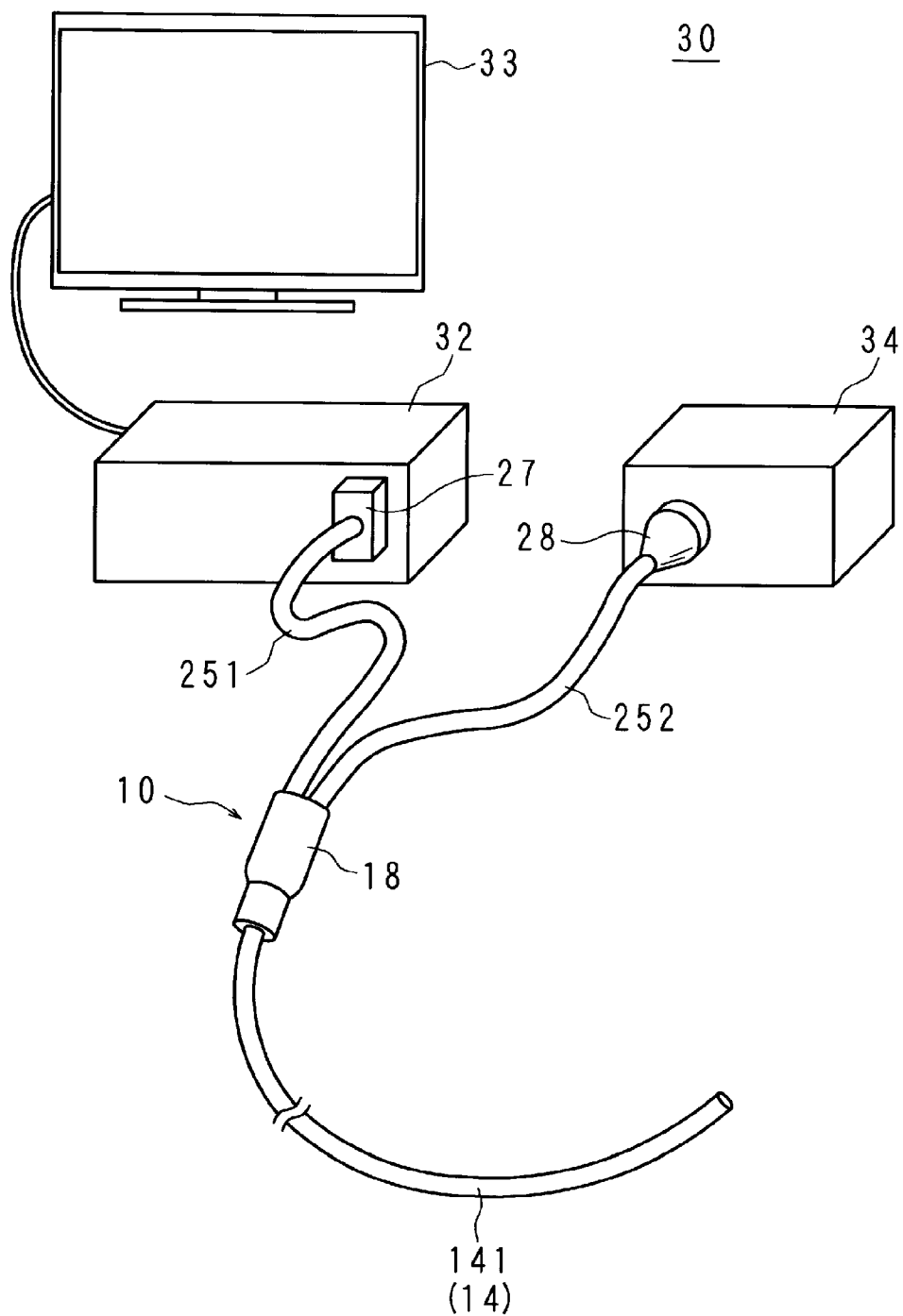
FIG. 1 is an exterior view of an endoscope system.

FIG. 1 is an exterior view of an endoscope system 30. The endoscope system 30 includes an endoscope 10, an endoscope processor 32, a light source device 34, and a display device 33. The display device 33 is connected to the endoscope processor 32. The endoscope 10 includes an insertion portion 14 covered with an exterior tube 141, a branch 18, a first cord covered with a first tube 251, and a second cord covered with a second tube 252. The insertion portion 14, the first cord, and the second cord are flexible.

The exterior tube 141, the first tube 251, and the second tube 252 communicate with each other at the branch 18. A scope connector 27 connected to the endoscope processor 32 is provided at the end portion of the first tube 251. A light guide connector 28 connected to the light source device 34 is provided at the end portion of the second tube 252. The scope connector 27 is an example of a first connector of this embodiment, and the light guide connector 28 is an example of a second connector of this embodiment.

Figure 2:
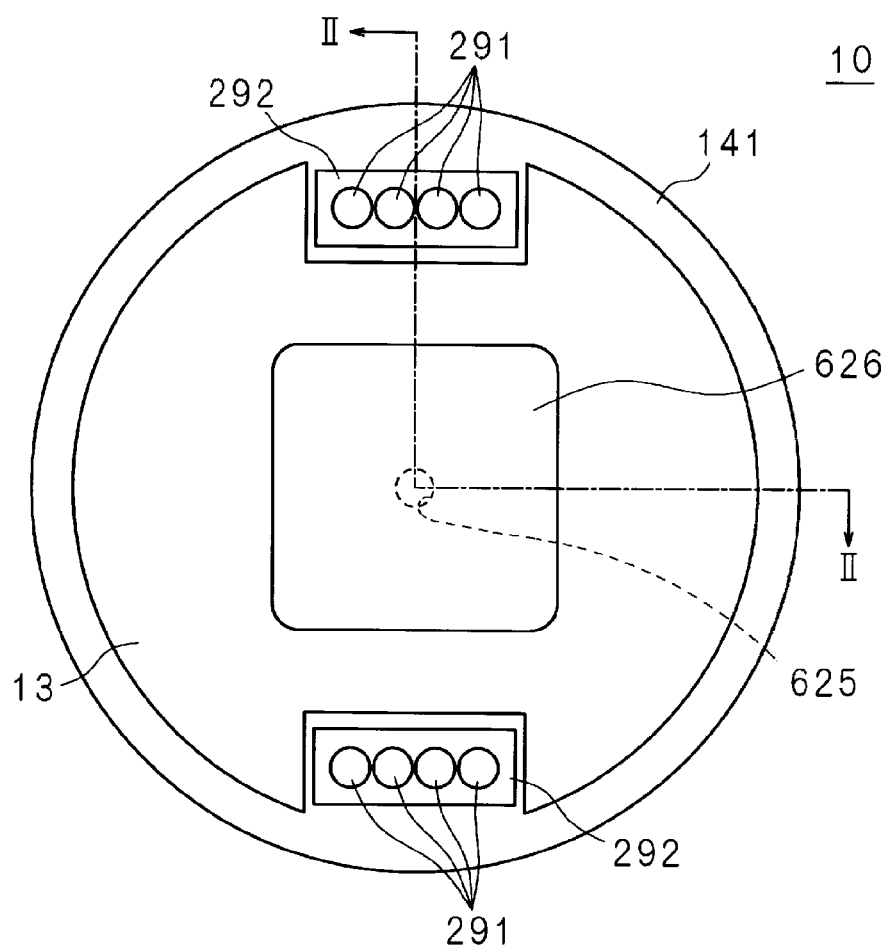
FIG. 2 is an exterior view of a tip of an endoscope.
Figure 3:
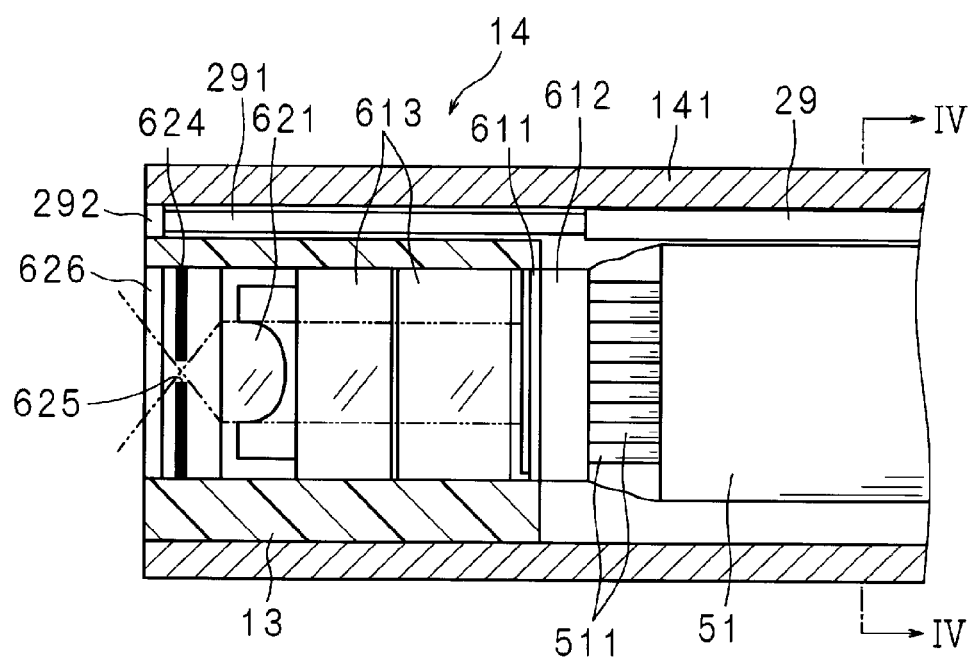
FIG. 3 is a partial cross-sectional view of the endoscope taken along line II-II of FIG. 2.
Figure 4:
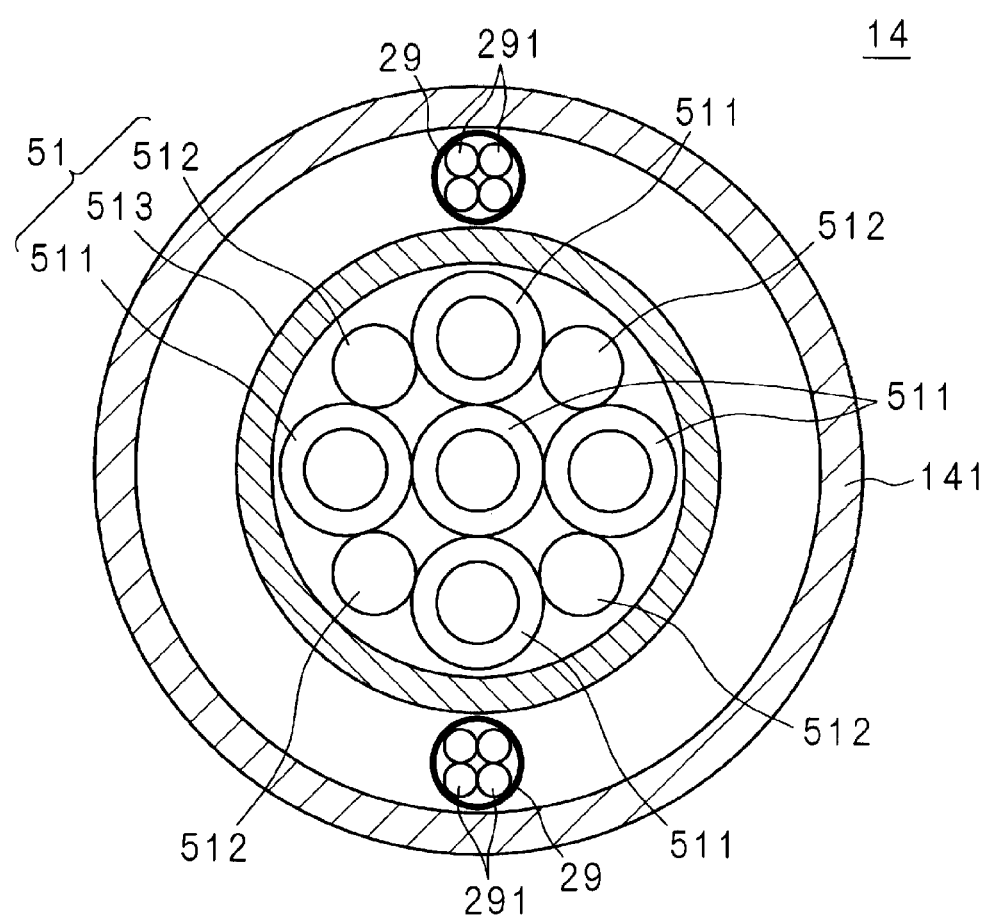
FIG. 4 is a cross-sectional view of an insertion portion taken along line IV-IV in FIG. 3.
Figure 5:
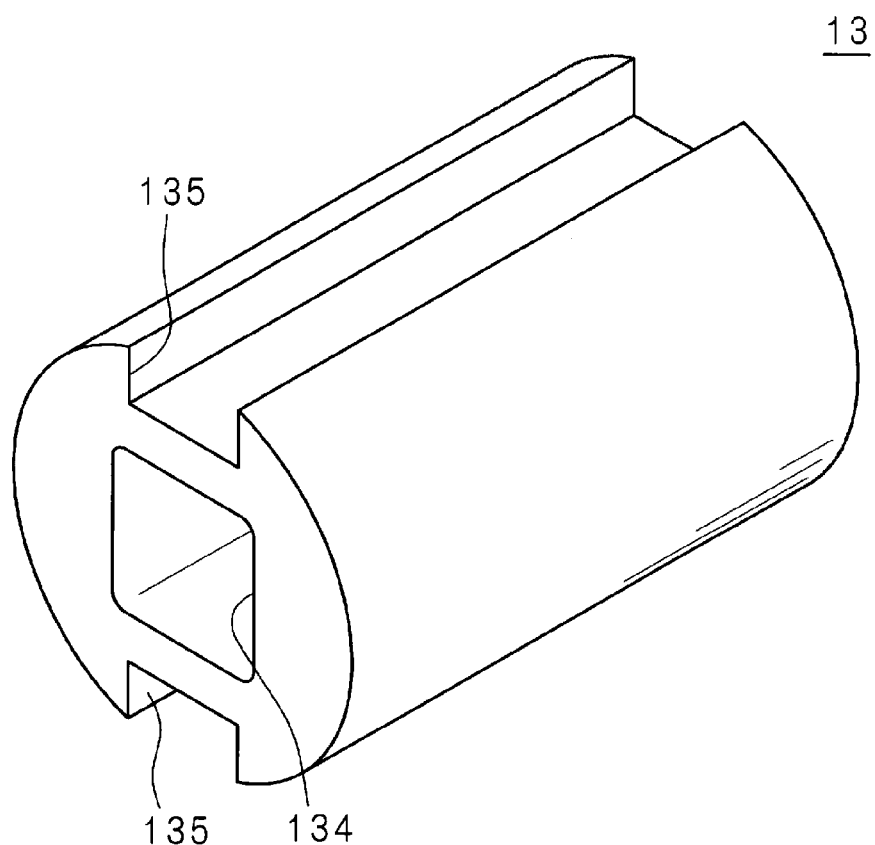
FIG. 5 is a perspective view of a tip frame.

FIG. 2 is an exterior view of the tip of the endoscope 10. FIG. 3 is a partial cross-sectional view of the endoscope 10 taken along line II-II of FIG. 2. FIG. 4 is a cross-sectional view of the insertion portion 14 taken along line IV-IV in FIG. 3. FIG. 5 is a perspective view of a tip frame 13.

The tip frame 13 is fixed to the tip of the exterior tube 141. As illustrated in FIG. 5, the tip frame 13 has a substantially cylindrical shape provided with a substantially square through hole 134 in the longitudinal direction. On the outside of the two opposing inner surfaces of the through holes 134, a substantially U-shaped light guide groove 135 that opens to the outer surface is provided.

Inside the through hole 134, a cover 626, a light-shielding mask 624, an imaging lens 621, and two spacers 613 are arranged from the tip side. The spacer 613, the image sensor 611, and an image pickup board 612 are built up. The cover 626 and the spacer 613 are translucent. A mask hole 625 is provided in the center of the light-shielding mask 624.

The imaging lens 621 is a collimator lens, and causes a light ray passing through the mask hole 625 to enter an image sensor 611 substantially vertically through the spacer 613. That is, the light-shielding mask 624, the imaging lens 621, and the image sensor 611 form a pinhole camera. Due to the action of the collimator lens, light is vertically incident on each pixel constituting the image sensor 611, so that a bright image can be taken even at the end portion of the image sensor 611.

A fiber holder 292 is fixed between the light guide groove 135 and the exterior tube 141. Four light guide fibers 291 are fixed in a row to the fiber holder 292. The configuration of the fiber holder 292 will be described later.

As illustrated in FIG. 4, in the insertion portion 14, a cable bundle 51 and two light guides 29 are inserted inside the exterior tube 141. The cable bundle 51 includes five cable strands 511 and four reinforcing wires 512, which are covered with a cable sheath 513.

The cable strand 511 has a configuration in which the outside of a conductor such as a copper wire is covered with an insulating coating. The cable strand 511 used for transmitting and receiving signals may be a coaxial cable. The cable strand 511 is connected to the image sensor 611 via the image pickup board 612. The reinforcing wire 512 is, for example, a yarn obtained by twisting aramid fibers.

For example, pins for connecting the cable strands 511 are erected in the image pickup board 612, and the cable strands 511 are connected to the respective pins by a method such as soldering. An insulating adhesive is applied to the connection between the cable strand 511 and the pin.

A connector may be connected to each of the image pickup board 612 and the end portion of the cable strand 511. By fitting both connectors, the image pickup board 612 and the cable strand 511 are connected.

Figure 6:
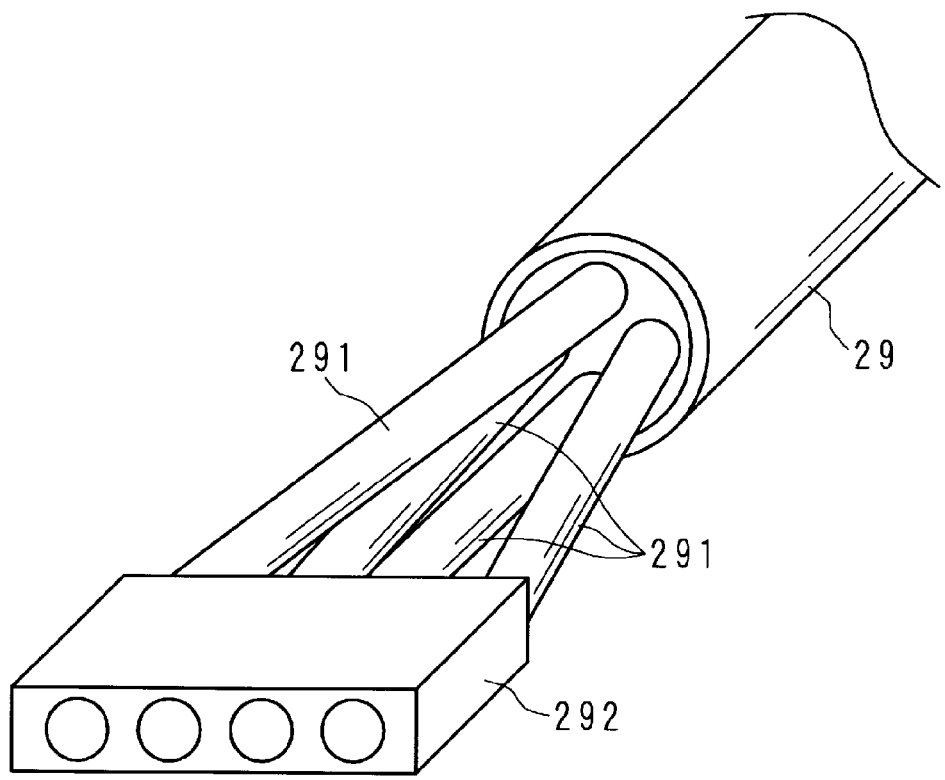
FIG. 6 is a perspective view illustrating a fiber holder and a light guide fiber.

As illustrated in FIG. 4, the light guide 29 has a configuration in which four light guide fibers 291 are covered with a coating. FIG. 6 is a perspective view illustrating the fiber holder 292 and the light guide fiber 291. The light guide fiber 291 is an example of the illumination fiber of this embodiment.

The coating of the light guide 29 is removed on the tip side of the insertion portion 14, and the light guide fiber 291 is exposed. The light guide fiber 291 is fixed to the fiber holder 292 in a state of being arranged in a row.

Figure 7:
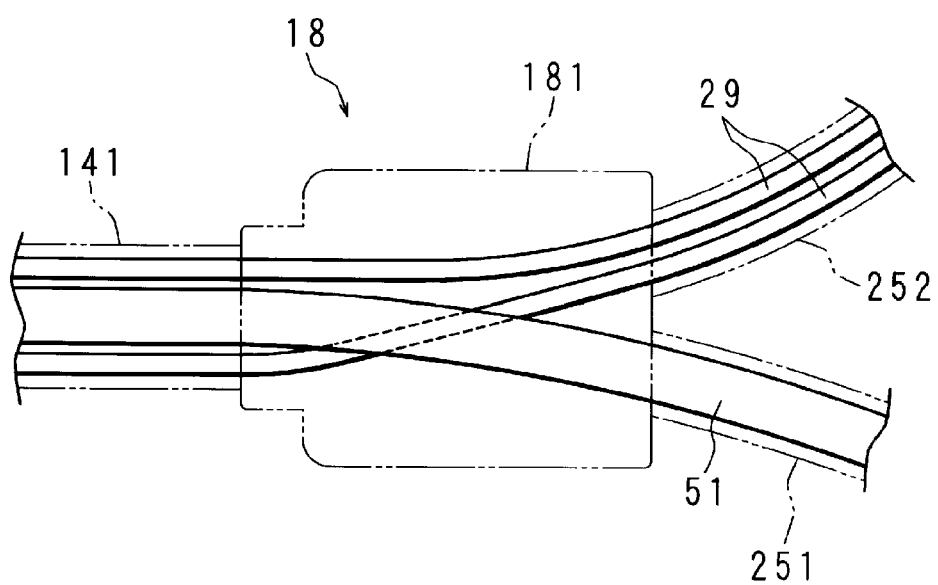
FIG. 7 is an explanatory diagram for explaining a configuration of a branch.

FIG. 7 is an explanatory diagram for explaining the configuration of the branch 18. The branch 18 includes a branch portion 181. The branch portion 181 is a hollow member having three openings. The exterior tube 141, the first tube 251, and the second tube 252 are connected to the opening, respectively, forming a substantially Y shape.

As described above, the cable bundle 51 and two light guides 29 are inserted inside the exterior tube 141. The cable bundle 51 and the light guide 29 are separated at the branch 18. The cable bundle 51 is inserted in the first tube 251 and the two light guides 29 are inserted in the second tube 252.

The insertion portion 14 has an outer diameter of 1 mm or less and 0.5 mm or more. For example, when the outer diameter of the insertion portion 14 is 1 mm, the wall thickness of the exterior tube 141 is a little over 0.1 mm, and the inner diameter of the exterior tube 141 is about 0.7 mm to 0.8 mm. When the cross-sectional shapes of the insertion portion 14 and the exterior tube 141 are not circular, the outer diameter and the inner diameter are determined by averaging the maximum diameter and the minimum diameter.

The image sensor 611 has a substantially square plate shape in which one side is half the length of the outer diameter of the insertion portion 14. For example, when the outer diameter of the insertion portion 14 is 1 mm, the image sensor 611 has a side of about 0.4 mm to 0.5 mm, that is, about 40% to 50% of the outer diameter of the insertion portion 14. The image pickup board 612 is a substantially square substrate having the same size as or one size larger than the image sensor 611.

The image pickup board 612 is provided with an electrode pad for connecting the image sensor 611. The image pickup board 612 may be a component-embedded board having a built-in driver IC or the like for driving the image sensor 611.

When the outer diameter of the insertion portion 14 is 0.5 mm, the wall thickness of the exterior tube 141 is about 0.1 mm, the inner diameter of the exterior tube 141 is about 0.2 mm to 0.3 mm. The image sensor 611 has a side of about 0.14 mm to 0.2 mm. The image sensor 611 is not limited to a square. For example, the image sensor 611 having any shape such as a rectangle or an octagon can be used.

The number of light guide fibers 291 included in the light guide 29 is an example. Similarly, the number of cable strands 511 and the number of reinforcing wires 512 included in the cable bundle 51 are also examples. The cable strand 511 used for the signal line may be a coaxial cable. The cable strand 511 used for the signal line may be a so-called twisted pair cable in which a set of two wires is twisted inside the cable bundle 51.

As illustrated in FIG. 3, the exterior tube 141 is watertightly joined to the tip frame 13 and the fiber holder 292 at the tip. Therefore, the insertion portion 14 has a rigid portion having a length of about twice the diameter from the tip.

As illustrated in FIG. 4, some space is secured inside the exterior tube 141 in the portion other than the tip. Therefore, the insertion portion 14 is flexible and can be flexed along the channel of the parent endoscope and the lumen to be observed.

Figure 8:
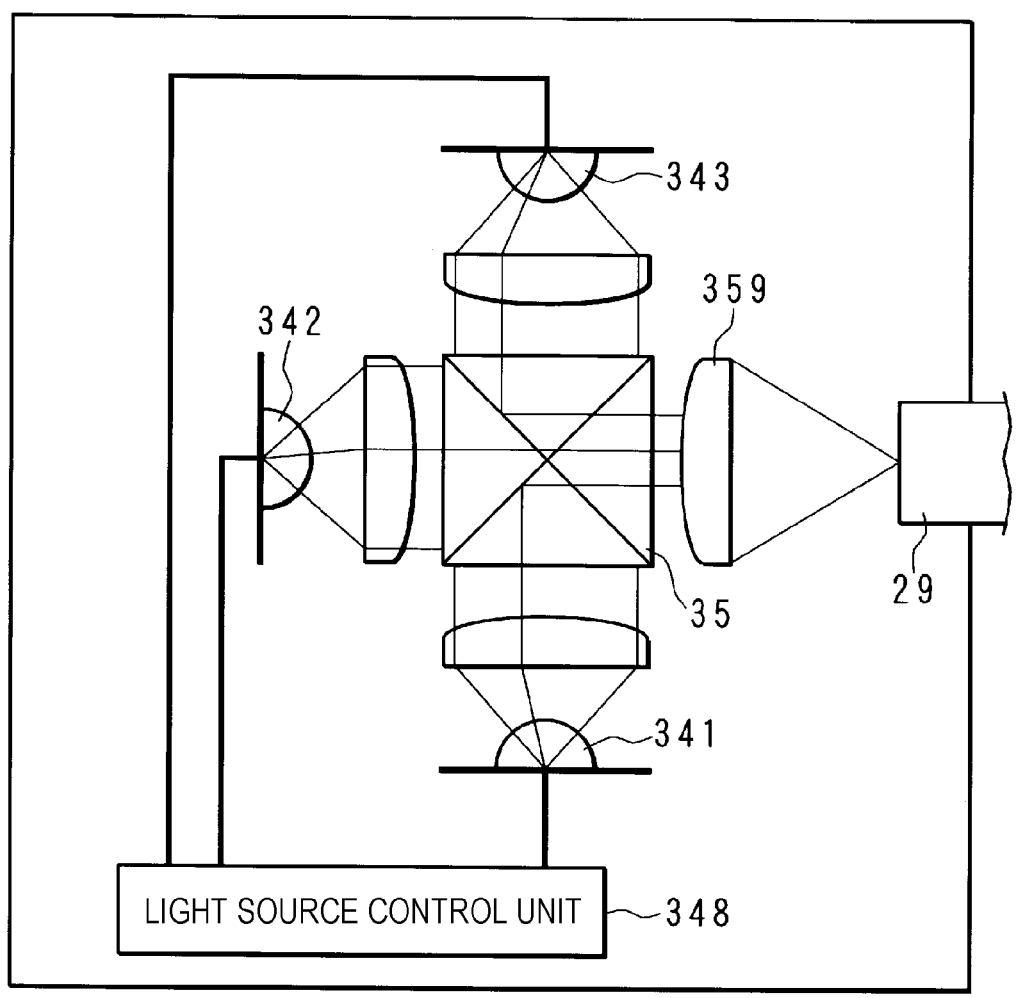
FIG. 8 is an explanatory diagram for explaining a configuration of a light source device.

FIG. 8 is an explanatory diagram for explaining the configuration of the light source device 34. The light source device 34 includes three light sources of a first lamp 341, a second lamp 342, and a third lamp 343, a prism 35, and a condenser lens 359.

The three light sources are, for example, LEDs (Light Emitting Diodes) that emit different colors. For example, the first lamp 341 is a red LED, the second lamp 342 is a green LED, and the third lamp 343 is a blue LED. The first lamp 341 may be a near-infrared LED. The third lamp 343 may be an ultraviolet LED.

The first lamp 341, the second lamp 342, and the third lamp 343 are connected to a light source control unit 348, respectively. The light source control unit 348 controls the emission intensity of each light source.

The prism 35 is a cross dichroic prism that emits light, which is emitted from three surfaces, from one surface. The light emitted from the first lamp 341, the second lamp 342, and the third lamp 343 becomes parallel light through the collimator lens, and is vertically incident on the incident surface of the prism 35.

The parallel light emitted from the prism 35 enters the end face of the light guide 29 connected to the light source device 34 via the condenser lens 359.

The outline of the usage of the endoscope 10 according to this embodiment will be described with reference to FIGS. 1 to 8. The user inserts the insertion portion 14 into the channel of the parent endoscope that has been inserted into a patient. A guide tube or the like may be used instead of the parent endoscope. The insertion portion 14 protrudes from the tip of the channel of the parent endoscope, and can be inserted to the peripheral portion that cannot be inserted by the thickness of the parent endoscope.

The illumination light emitted from the light source device 34 is emitted from the tip of the insertion portion 14 via the light guide fiber 291. The range illuminated by the illumination light is photographed by the image sensor 611 through the mask hole 625 and the imaging lens 621. A video signal is transmitted from the image sensor 611 to the endoscope processor 32 via the cable strand 511. The video signal is processed by the endoscope processor 32, and the video is displayed on the display device 33.

As described above, since the light-shielding mask 624, the imaging lens 621, and the image sensor 611 form a pinhole camera, the image sensor 611 can capture an image having a deep depth of focus. Therefore, it is possible to take an image suitable for observing a narrow lumen.

The user can adjust the light emitted from the light source device 34 through a touch panel or a switch (not illustrated). The light source device 34 may be controlled via the endoscope processor 32.

For example, when the user observes with white light, the light source control unit 348 adjusts the balance of the amount of light of the first lamp 341 to the third lamp 343 so that the light emitted from the tip of the light guide fiber 291 becomes white light.

When performing near infrared photo-immunotherapy (NIR-PIT), an antibody drug that specifically binds to cancer cells should be administered to the patient in advance. A light absorber (IR700) is attached to the antibody drug.

After observing the affected area with the endoscope 10, the user instructs the irradiation of light for the near infrared photo-immunotherapy. The light source control unit 348 adjusts the balance of the amount of light of the first lamp 341 to the third lamp 343 so that the light emitted from the tip of the light guide fiber 291 becomes the near-infrared ray.

The light source control unit 348 preferably adjusts the balance of the amount of light of the first lamp 341 to the third lamp 343 so that the light for the near infrared photo-immunotherapy and the white light for observation are emitted from the tip of the light guide fiber 291 at the same time. The user can irradiate the target site with light for the near infrared photo-immunotherapy by adjusting the tip position of the insertion portion 14 so that the target site is illuminated by the illumination light.

By using the near infrared photo-immunotherapy, it is expected that only cancer cells can be accurately killed and cancer treatment with few side effects can be realized.

When performing photodynamic diagnosis (PDD), 5-aminolevulinic acid (5-ALA) should be administered to the patient in advance. When 5-ALA is administered, protoporphyrin IX (PpIX) accumulates in cancer cells. The user instructs the irradiation of light for photodynamic diagnosis. The light source control unit 348 adjusts the balance of the amount of light of the first lamp 341 to the third lamp 343 so as to irradiate blue light having a wavelength of 375 nm to 445 nm from the tip of the light guide fiber 291.

When the field of view under observation contains cancer cells in which protoporphyrin IX has accumulated, red fluorescence having a wavelength of 600 nm to 740 nm is emitted. Therefore, the user can easily detect the cancer.

The user may perform photodynamic therapy (PDT) following the photodynamic diagnosis. The user instructs the irradiation of light for photodynamic therapy. The light source control unit 348 adjusts the balance of the amount of light of the first lamp 341 to the third lamp 343 so that red light having a wavelength of 600 nm to 740 nm or green light having a wavelength of 480 nm to 580 nm is emitted from the tip of the light guide fiber 291. The light source control unit 348 may irradiate the tip of the light guide fiber 291 with light that is a mixture of red light and green light.

Protoporphyrin IX is excited by irradiated red and green light to generate active oxygen. Cancer cells in which protoporphyrin IX has accumulated are damaged by the generated active oxygen and die. By using photodynamic diagnosis and photodynamic therapy, it is expected that cancer cells can be reliably detected and accurately killed, and cancer treatment with few side effects can be realized.

According to this embodiment, a small diameter endoscope 10 can be provided. For example, a bronchial endoscope having a channel inner diameter of a little over 1 mm, a urinary endoscope, or the like can be used as a parent endoscope, and peripheral parts that cannot be reached by these parent endoscopes can be observed.

It is also possible to observe the inside of the pancreatic bile duct by using a duodenal endoscope having an elevator as a parent endoscope. Since the insertion portion 14 can be easily inserted into the nipple sphincter muscle without performing endoscopic sphincteropapillotomy (EST), the invasion to the patient can be reduced.

According to this embodiment, by using a pinhole camera, it is possible to provide the endoscope 10 having a deep depth of focus and capable of observing from the vicinity of the tip of the insertion portion 14 to the depth of the lumen. Further, by using a pinhole camera, it is possible to provide the endoscope 10 which has a simple structure and is easy to assemble. Therefore, the low-cost endoscope 10 can be provided.

Instead of the pinhole camera, a normal observation optical system that forms an image on the image sensor 611 using an objective lens may be used. By doing so, it is possible to provide the endoscope 10 capable of capturing a brighter image than when using a pinhole camera.

According to this embodiment, it is possible to provide the endoscope system 30 that can be used for both normal white light observation and the near infrared photo-immunotherapy. Since a tumor generated in the peripheral part can be reliably irradiated with near-infrared light, improvement in the therapeutic effect can be expected.

According to this embodiment, it is possible to provide the endoscope system 30 that can be used for both observation with normal white light and photodynamic diagnosis and photodynamic therapy. Since a tumor generated in the peripheral part can be reliably detected by photodynamic diagnosis and can be irradiated with the excitation light required for photodynamic therapy, early detection and early treatment can be expected.

According to this embodiment, since the light emitted from a plurality of light sources is used in combination, the endoscope system 30 that irradiates bright illumination light can be provided. It can be observed by illuminating the interior of the lumen with sufficient brightness.

The endoscope system 30 may be a so-called frame sequential method in which the color of the light source emitted by the light source device 34 is switched at high speed. Even if a small image sensor 611 is used, it is possible to provide the endoscope system 30 that can obtain a high-resolution image.

Second Embodiment

This embodiment relates to the endoscope 10 in which the light guide fibers 291 are distributed around the cable bundle 51. Descriptions regarding common parts with the first embodiment will be omitted.

Figure 9:
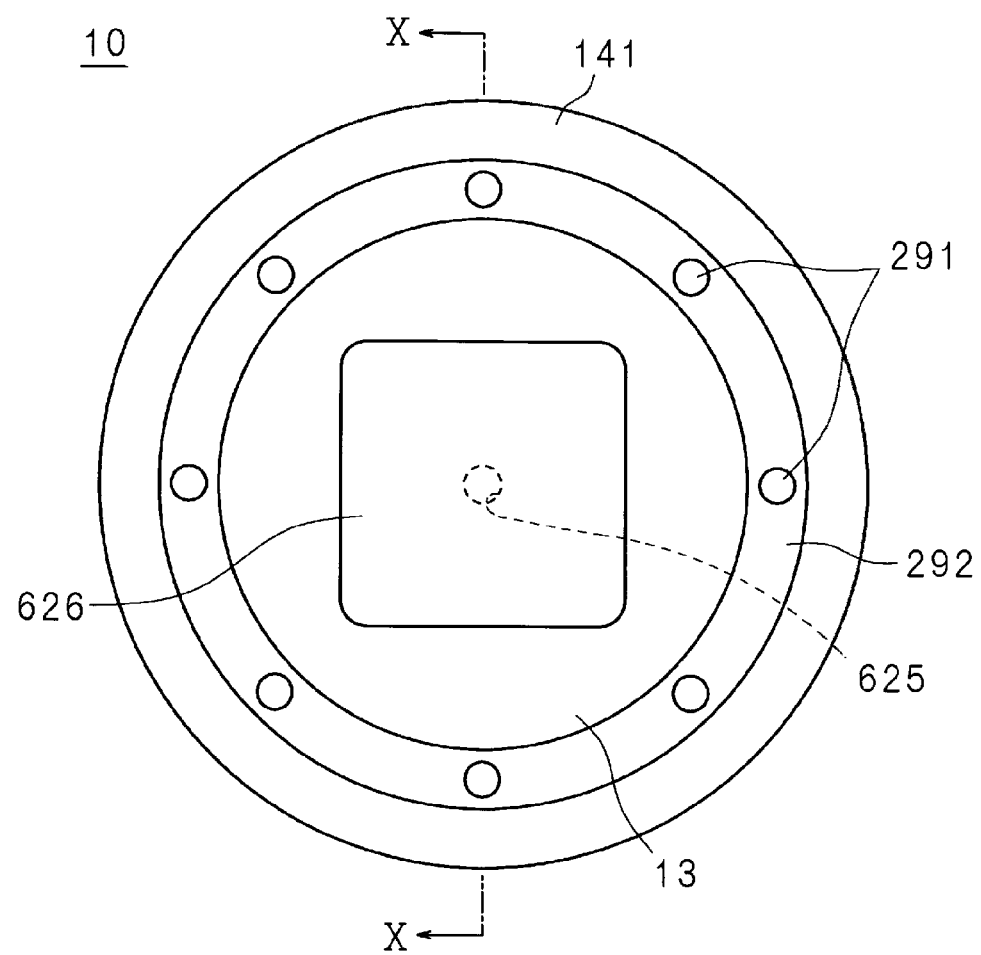
FIG. 9 is an exterior view of the tip of the endoscope according to a second embodiment.
Figure 10:
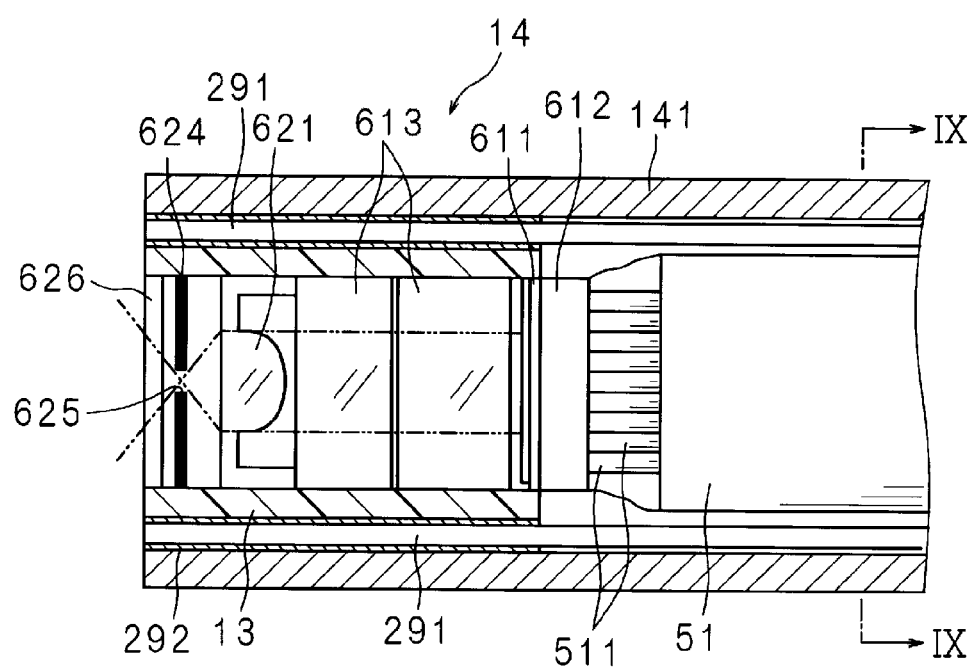
FIG. 10 is a partial cross-sectional view of the endoscope taken along line X-X of FIG. 9.
Figure 11:
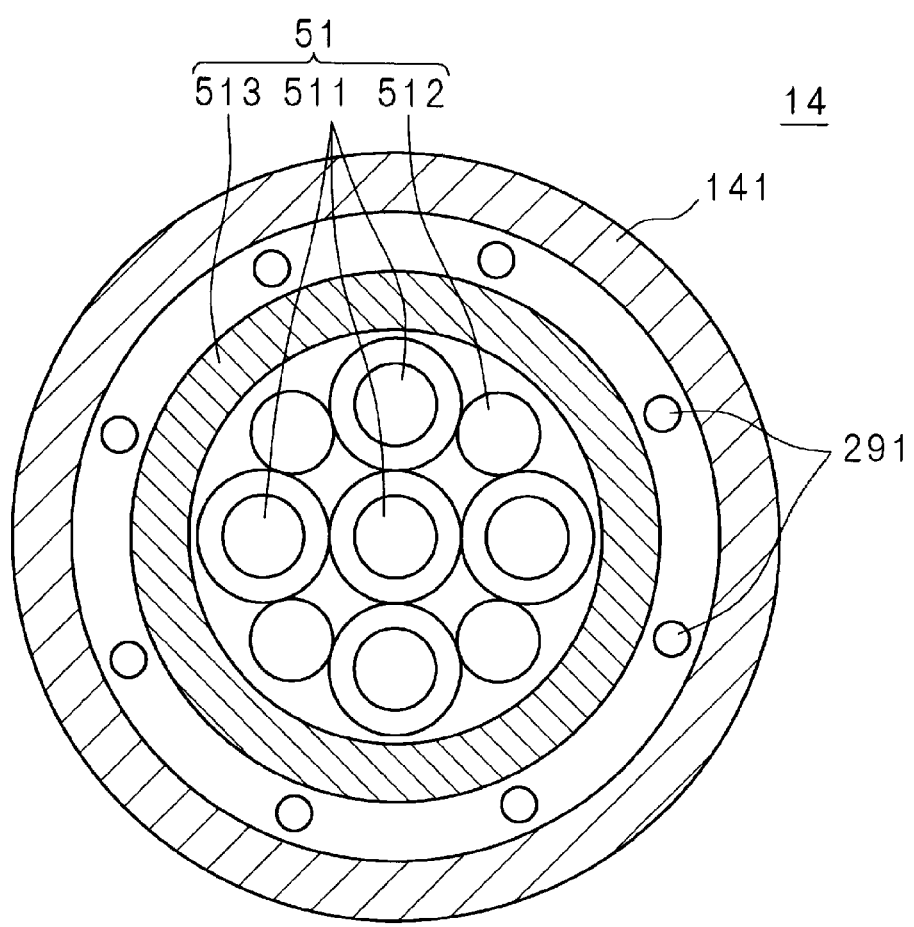
FIG. 11 is a cross-sectional view of the insertion portion taken along line IX-IX of FIG. 10.

FIG. 9 is an exterior view of the tip of the endoscope 10 according to the second embodiment. FIG. 10 is a partial cross-sectional view of the endoscope 10 taken along line X-X of FIG. 9. FIG. 11 is a cross-sectional view of the insertion portion 14 taken along line IX-IX of FIG. 10.

The tip frame 13 is fixed to the tip of the exterior tube 141. The tip frame 13 has a substantially cylindrical shape provided with a substantially square through hole 134 in the longitudinal direction. The outer circumference of the tip frame 13 is covered with a pipe-shaped fiber holder 292. As illustrated in FIG. 9, the end surfaces of the light guide fibers 291 are evenly arranged on the end surface of the fiber holder 292.

As illustrated in FIG. 11, in the insertion portion 14, the light guide fiber 291 is arranged so as to surround the cable bundle 51. The light guide fiber 291 may be parallel to the cable bundle 51 or may be spirally wound around the cable bundle 51.

According to this embodiment, since the light guide fibers 291 are not bundled, the insertion portion 14 which is thinner than that of the first embodiment can be realized. Further, the endoscope 10 using the thick cable strand 511 can be realized by the insertion portion 14 having the same thickness as that of the first embodiment. By using a thick cable strand 511, it is possible to provide the endoscope system 30 that displays an image with less noise.

According to this embodiment, since the illumination light is radiated from the entire circumference of the end portion of the insertion portion 14, it is possible to provide the endoscope 10 that does not generate unnecessary shadows and can obtain a good observation field of view.

Third Embodiment

This embodiment relates to the endoscope system 30 using the light source device 34 having a light source of five colors. Descriptions regarding common parts with the first embodiment will be omitted.

Figure 12:
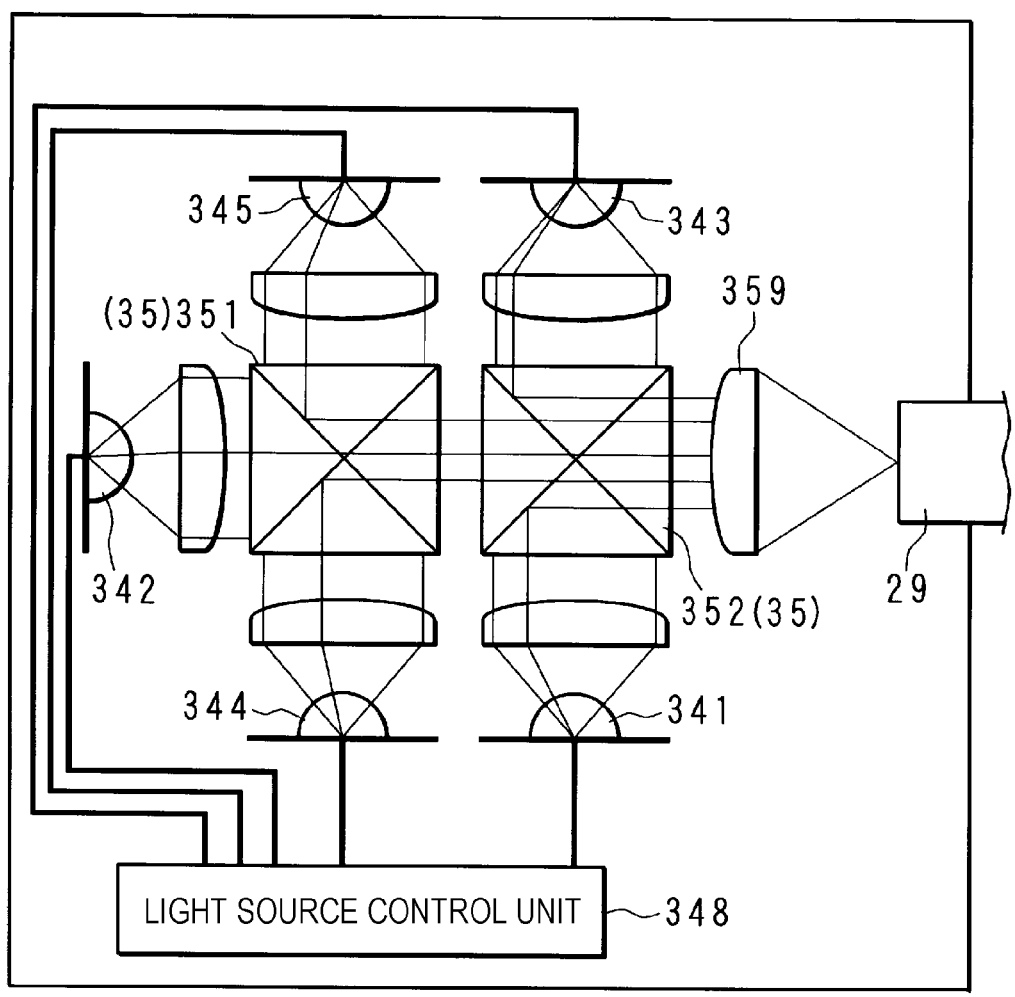
FIG. 12 is an explanatory diagram for explaining a configuration of the light source device according to a third embodiment.

FIG. 12 is an explanatory diagram for explaining the configuration of the light source device 34 according to the third embodiment. The light source device 34 includes five light sources of the first lamp 341, the second lamp 342, the third lamp 343, a fourth lamp 344, and a fifth lamp 345, and two prisms 35 of the first prism 351 and the second prism 352, and the condenser lens 359.

The five light sources are, for example, LEDs that emit different colors. For example, the first lamp 341 is a red LED, the second lamp 342 is a broadband green LED, the third lamp 343 is a broadband blue LED, the fourth lamp 344 is a narrow band green LED, and the fifth lamp 345 is a narrow band blue LED. The first lamp 341 may be a near-infrared LED. The third lamp 343 may be an ultraviolet LED.

The first lamp 341, the second lamp 342, the third lamp 343, the fourth lamp 344, and the fifth lamp 345 are each connected to the light source control unit 348. The light source control unit 348 controls the emission intensity of each light source. The first prism 351 and the second prism 352 are cross dichroic prisms.

The light emitted from the second lamp 342, the fourth lamp 344, and the fifth lamp 345 becomes parallel light through the collimator lens and is vertically incident on the incident surface of the first prism 351. The parallel light emitted from the first prism 351 is vertically incident on one incident surface of the second prism 352. The light emitted from the first lamp 341 and the third lamp 343 becomes parallel light through the collimator lens, respectively, and is vertically incident on the other incident surfaces of the second prism 352.

The parallel light emitted from the second prism 352 enters the end surface of the light guide 29 connected to the light source device 34 via the condenser lens 359.

For example, when the user observes with white light, the light source control unit 348 adjusts the balance of the amount of light of the first lamp 341 to the fifth lamp 345 so that the light emitted from the tip of the light guide fiber 291 becomes white light.

For example, when the user observes with a blood vessel-enhanced image, the light source control unit 348 adjusts the balance of the amount of light of the first lamp 341 to the fifth lamp 345 so that the light emitted from the tip of the light guide fiber 291 becomes a mixed light of purple and green. The endoscope processor 32 processes the video signal acquired by the image sensor 611, and the blood vessel-enhanced image is displayed in the display device 33.

According to this embodiment, it is possible to provide the endoscope system 30 capable of performing various observations and treatments by using a light source of five colors.

Fourth Embodiment

This embodiment relates to the endoscope system 30 using the light source device 34 having a light source of seven colors. Descriptions regarding common parts with the first embodiment will be omitted.

Figure 13:
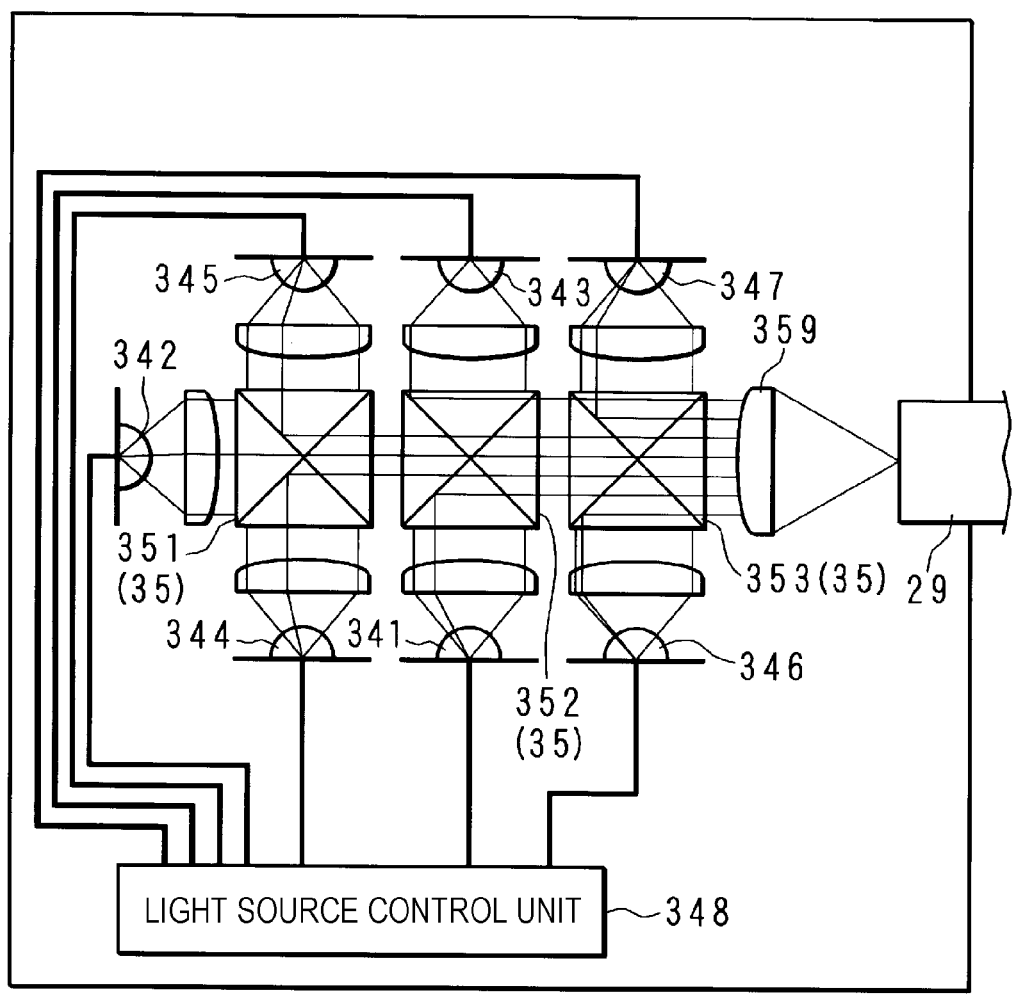
FIG. 13 is an explanatory diagram for explaining a configuration of the light source device according to a fourth embodiment.

FIG. 13 is an explanatory diagram for explaining the configuration of the light source device 34 according to the fourth embodiment. The light source device 34 includes seven light sources of the first lamp 341, the second lamp 342, the third lamp 343, the fourth lamp 344, the fifth lamp 345, a sixth lamp 346, and a seventh lamp 347, three prisms 35 of the first prism 351, the second prism 352, and a third prism 353, and the condenser lens 359.

The seven light sources are, for example, LEDs that emit different colors. For example, the first lamp 341 is a red LED, the second lamp 342 is a broadband green LED, the third lamp 343 is a broadband blue LED, the fourth lamp 344 is a narrow band green LED, the fifth lamp 345 is a narrow band blue LED, the sixth lamp 346 is a near-infrared LED, and the seventh lamp 347 is a ultraviolet LED.

The first lamp 341, the second lamp 342, the third lamp 343, the fourth lamp 344, the fifth lamp 345, the sixth lamp 346, and the seventh lamp 347 are connected to the light source control unit 348, respectively. The light source control unit 348 controls the emission intensity of each light source. The first prism 351, the second prism 352, and the third prism 353 are cross dichroic prisms.

The light emitted from the second lamp 342, the fourth lamp 344, and the fifth lamp 345 becomes parallel light through the collimator lens and is vertically incident on the incident surface of the first prism 351. The parallel light emitted from the first prism 351 is vertically incident on one incident surface of the second prism 352. The light emitted from the first lamp 341 and the third lamp 343 becomes parallel light through the collimator lens, respectively, and is vertically incident on the other incident surfaces of the second prism 352.

The parallel light emitted from the second prism 352 is vertically incident on one incident surface of the third prism 353. The light emitted from the sixth lamp 346 and the seventh lamp 347 becomes parallel light through the collimator lens, respectively, and is vertically incident on the other incident surface of the third prism 353. The parallel light emitted from the third prism 353 enters the end surface of the light guide 29 connected to the light source device 34 via the condenser lens 359.

According to this embodiment, it is possible to provide the endoscope system 30 capable of performing various observations and treatments by using a light source of seven colors.

Fifth Embodiment

This embodiment relates to the endoscope system 30 using the light source device 34 that uses a mirror instead of the prism 35. Descriptions regarding common parts with the first embodiment will be omitted.

Figure 14:
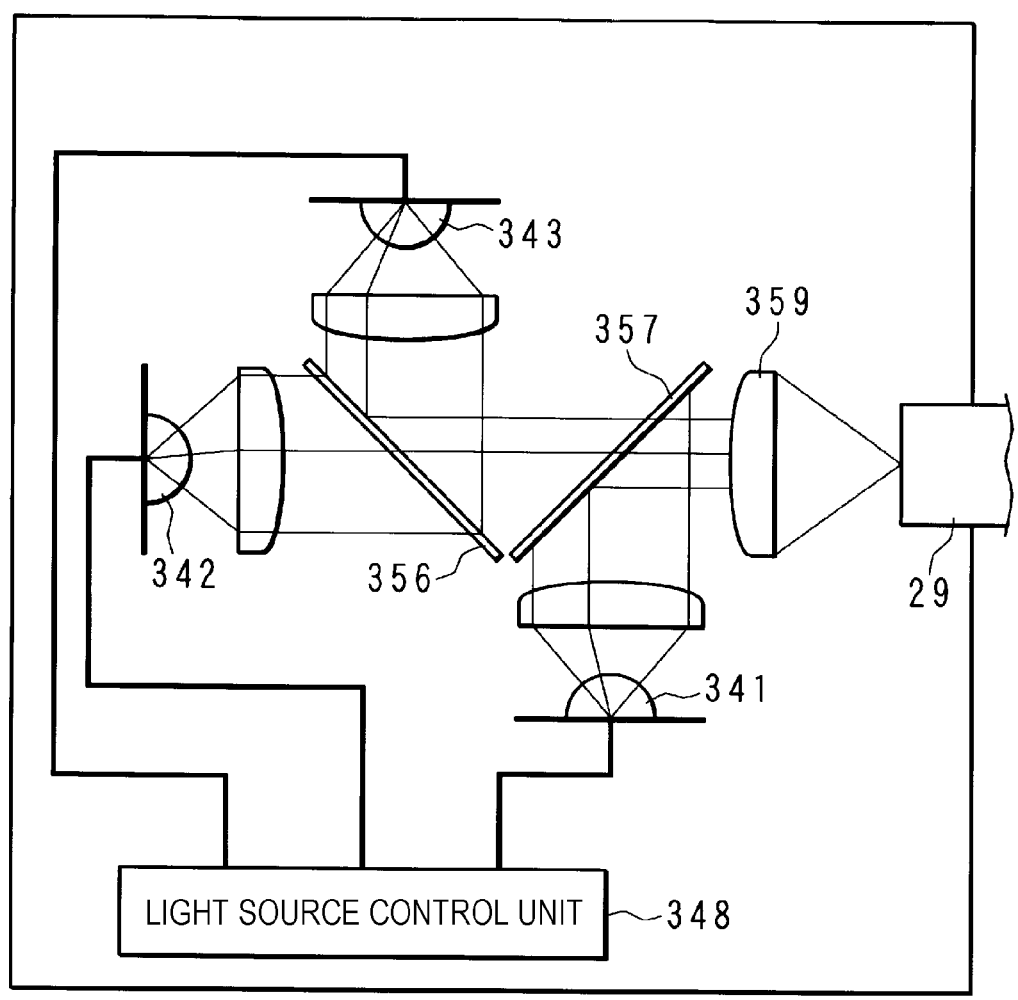
FIG. 14 is an explanatory diagram illustrating a configuration of the light source device according to a fifth embodiment.

FIG. 14 is an explanatory diagram for explaining the configuration of the light source device 34 according to the fifth embodiment. The light source device 34 includes three light sources of the first lamp 341, the second lamp 342, and the third lamp 343, two mirrors of a first mirror 356 and a second mirror 357, and the condenser lens 359.

The three light sources are, for example, LEDs whose emission colors are different. For example, the first lamp 341 is a red LED, the second lamp 342 is a green LED, and the third lamp 343 is a blue LED. The first lamp 341 may be a near-infrared LED. The third lamp 343 may be an ultraviolet LED.

The first lamp 341, the second lamp 342, and the third lamp 343 are connected to a light source control unit 348, respectively. The light source control unit 348 controls the emission intensity of each light source.

The first mirror 356 is a dichroic mirror that reflects light of a wavelength emitted from the third lamp 343 and transmits light of other wavelengths. The second mirror 357 is a dichroic mirror that reflects light of a wavelength emitted from the first lamp 341 and transmits light of other wavelengths. The first mirror 356 and the second mirror 357 are arranged orthogonally to each other.

The light emitted from the first lamp 341 becomes parallel light through the collimator lens, is obliquely incident on the second mirror 357, is reflected by the second mirror 357, and reaches the condenser lens 359. The light emitted from the second lamp 342 becomes parallel light through the collimator lens, passes through the first mirror 356 and the second mirror 357, and reaches the condenser lens 359.

The light emitted from the third lamp 343 becomes parallel light through the collimator lens, is obliquely incident on the first mirror 356, is reflected by the first mirror 356, passes through the second mirror 357, and reaches the condenser lens 359.

The light emitted from each light source and reaching the condenser lens 359 enters the end surface of the light guide 29 connected to the light source device 34 via the condenser lens 359.

According to this embodiment, since a mirror is used instead of the prism 35, it is possible to provide the endoscope system 30 including a lightweight and inexpensive light source device 34.

Sixth Embodiment

This embodiment relates to the endoscope 10 having a bending mechanism. Descriptions regarding common parts with the first embodiment will be omitted.

Figure 15:
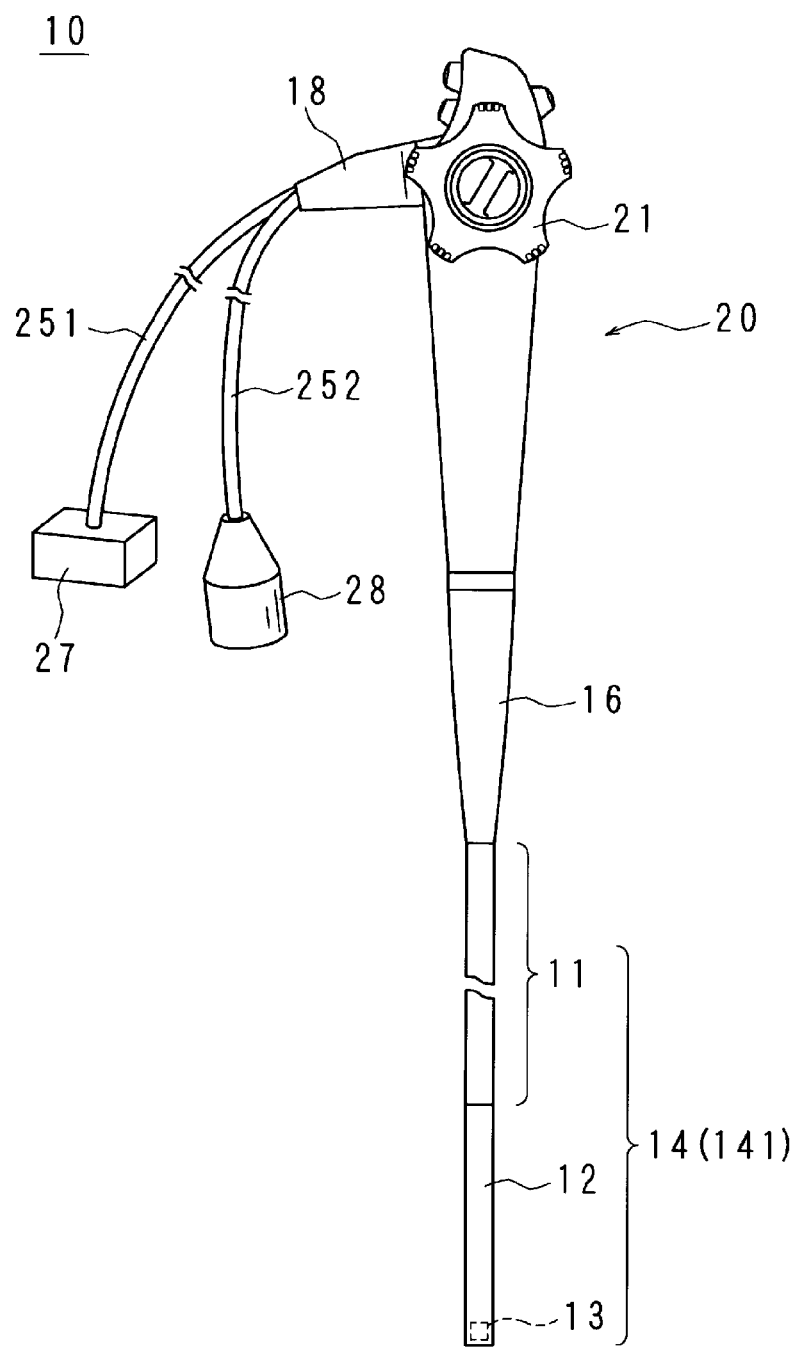
FIG. 15 is an exterior view of the endoscope according to a sixth embodiment.

FIG. 15 is an exterior view of the endoscope 10 of the sixth embodiment. The endoscope 10 of this embodiment includes the insertion portion 14 and an operation unit 20. The operation unit 20 is provided with a bending knob 21.

The insertion portion 14 is long and has one end connected to the operation unit 20 via a bending preventing portion 16. The insertion portion 14 is covered with the exterior tube 141, and has a soft portion 11, a bending section 12, and the tip frame 13 in this order from the operation unit 20 side. The bending section 12 is bent according to an operation of the bending knob 21.

The first cord covered with the first tube 251 and the second cord covered with the second tube 252 branch from the branch 18 protruding from the operation unit 20. The scope connector 27 is provided at the end portion of the first tube 251. The light guide connector 28 is provided at the end portion of the second tube 252.

Figure 16:
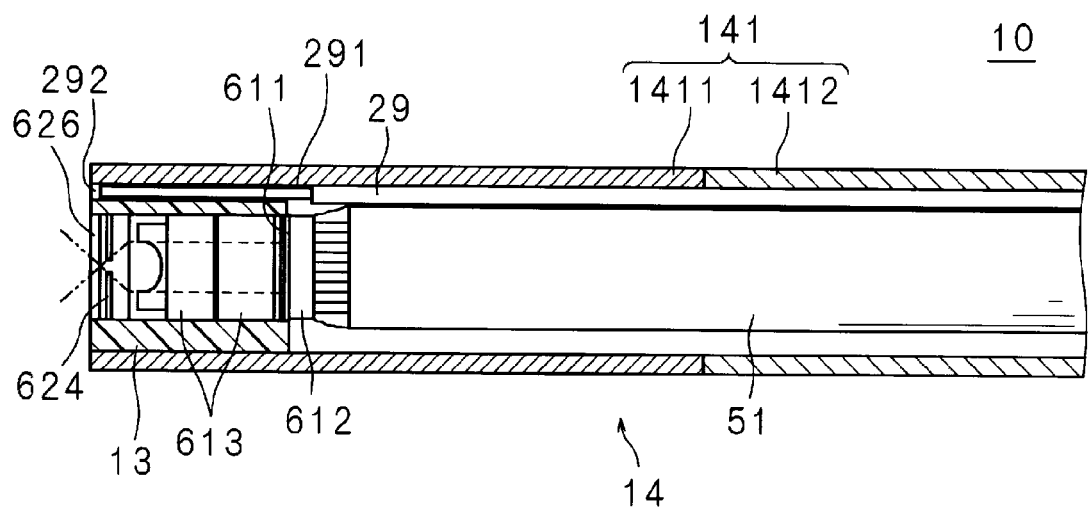
FIG. 16 is a partial cross-sectional view of the insertion portion according to the sixth embodiment.

FIG. 16 is a partial cross-sectional view of the insertion portion 14 according to the sixth embodiment. FIG. 16 illustrates a cross section similar to that of FIG. 3. The exterior tube 141 has a first region 1411 that is relatively easy to bend, and a second region 1412 that is less likely to bend than the first region 1411. The first region 1411 and the second region 1412 are integrally molded.

The first region 1411 is formed of a resin material having a low hardness, and the second region 1412 is formed of a resin material having a high hardness. The first region 1411 is a range of, for example, about 50 mm from the tip of the exterior tube 141.

The portion of the insertion portion 14 that is covered by the first region 1411 and does not include components such as the tip frame 13 inside forms the bending section 12 described with reference to FIG. 15. The portion of the insertion portion 14 covered by the second region 1412 forms the soft portion 11 also described with reference to FIG. 15.

Figure 17:
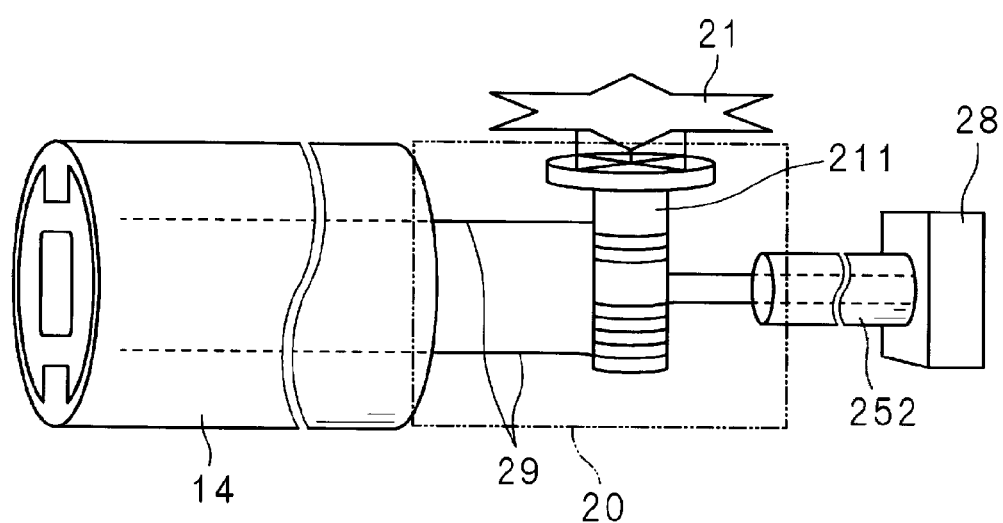
FIG. 17 is an explanatory diagram for explaining a configuration of an operation unit of the endoscope according to the sixth embodiment.

FIG. 17 is an explanatory diagram for explaining the configuration of the operation unit 20 of the endoscope 10 according to the sixth embodiment. In FIG. 17, the configuration around the bending knob 21 is schematically illustrated, and the branch 18, the first tube 251, and the scope connector 27 are not illustrated.

The bending knob 21 is rotatable about a bending shaft 211. Two light guides 29 are wound around the bending shaft 211 several times in opposite directions. The bending shaft 211 is an example of a traction portion of this embodiment.

When the user turns the bending knob 21 clockwise, the upper light guide 29 in FIG. 17 is wound around the bending knob 21 and the lower light guide 29 is unwound from the bending knob 21. Therefore, the upper light guide 29 is pulled and the lower light guide 29 is loosened. As a result, the bending section 12 is bent upward in FIG. 17.

When the user turns the bending knob 21 counterclockwise, the lower light guide 29 in FIG. 17 is wound around the bending knob 21 and the upper light guide 29 is unwound from the bending knob 21. Therefore, the lower light guide 29 is pulled and the upper light guide 29 is loosened. As a result, the bending section 12 is bent downward in FIG. 17.

According to this embodiment, since the light guide 29 also serves as a bending wire, it is possible to provide a small-diameter endoscope 10 having a bending mechanism.

Figure 19:
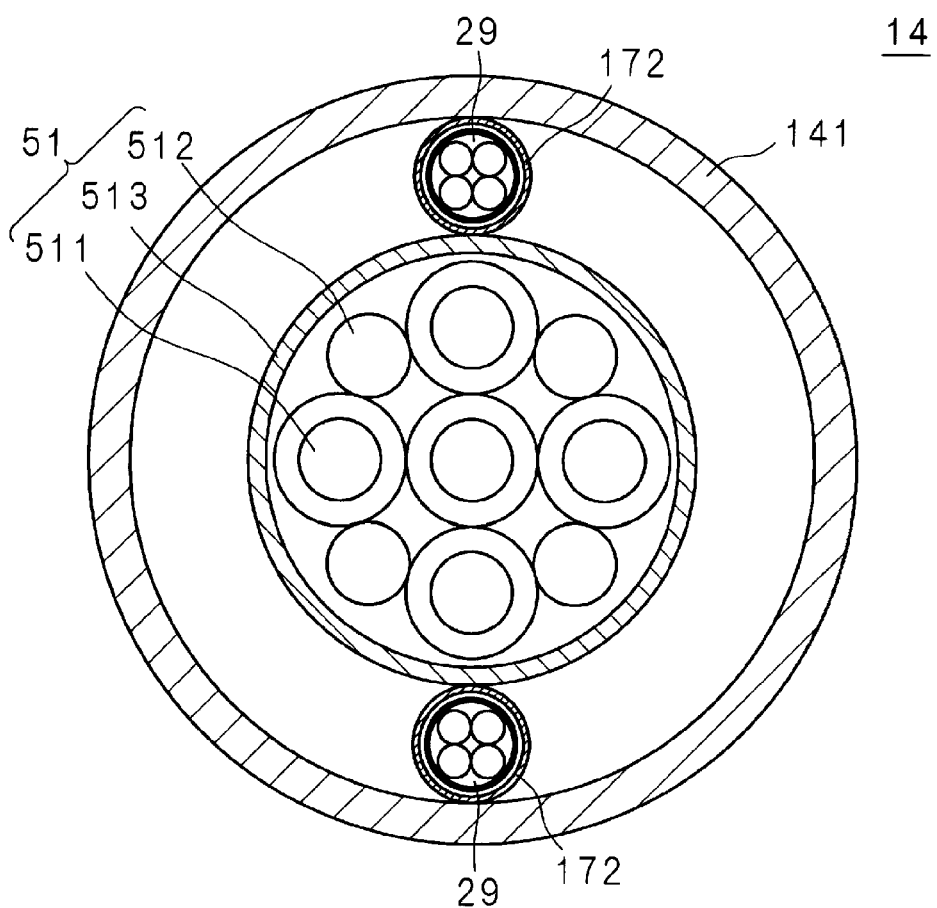
FIG. 19 is a partial cross-sectional view of the endoscope taken along line XIX-XIX of FIG. 18.

The configuration of the operation unit 20 described with reference to FIG. 17 is an example. The user can use any configuration that can be towed by selecting one of the two light guides 29. For example, the bending shaft 211 in FIG. 19 is swingably supported in the plane of FIG. 17 at the central portion in the longitudinal direction, and a grip portion that can be gripped by the user may be provided at the tip of the bending shaft 211 instead of the bending knob 21.

When the user swings the bending shaft 211 clockwise in FIG. 17, the bending section 12 bends upward in FIG. 17. When the user swings the bending shaft 211 counterclockwise in FIG. 17, the bending section 12 bends downward in FIG. 17.

Only any one of the light guides 29 may be towable by the user. It is possible to provide a so-called unidirectionally bending endoscope 10, which can be bent only in one direction.

Seventh Embodiment

Figure 18:
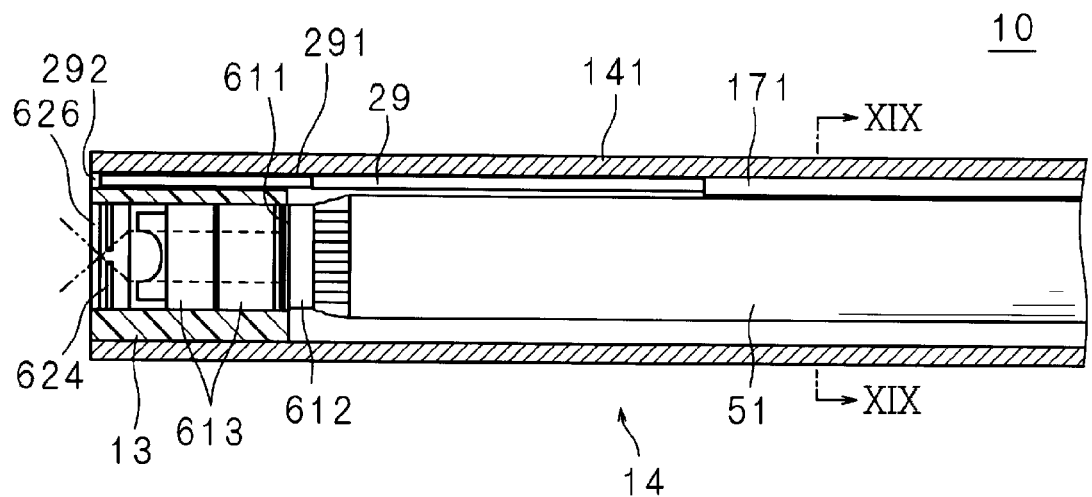
FIG. 18 is a partial cross-sectional view of the endoscope according to a seventh embodiment.

This embodiment relates to the endoscope 10 in which the light guide 29 is inserted into a bending guide tube 172. Descriptions regarding common parts with the sixth embodiment will be omitted. FIG. 18 is a partial cross-sectional view of the endoscope 10 according to the seventh embodiment. FIG. 18 illustrates a cross section similar to that of FIG. 16. FIG. 19 is a partial cross-sectional view of the endoscope 10 taken along line XIX-XIX of FIG. 18.

The exterior tube 141 of this embodiment is entirely made of one kind of resin material. As illustrated in FIG. 19, the light guide 29 is inserted into a tubular bending guide tube 172. The tip of the bending guide tube 172 is located, for example, about 50 mm from the tip of the insertion portion 14.

The portion of the insertion portion 14 in which the bending guide tube 172 does not exist is more likely to bend than the portion in which the bending guide tube 172 exists. The portion of the insertion portion 14 in which the bending guide tube 172 does not exist forms the bending section 12. The portion of the insertion portion 14 in which the bending guide tube 172 exists forms the soft portion 11.

According to this embodiment, the exterior tube 141 can be created by appropriately cutting a long tube that is uniform over the entire length. Therefore, it is possible to provide the endoscope 10 with a small amount of waste members during manufacturing.

Eighth Embodiment

This embodiment relates to the endoscope 10 in which the bending section 12 is bent by using the cable bundle 51. Descriptions regarding common parts with the sixth embodiment will be omitted.

Figure 20:
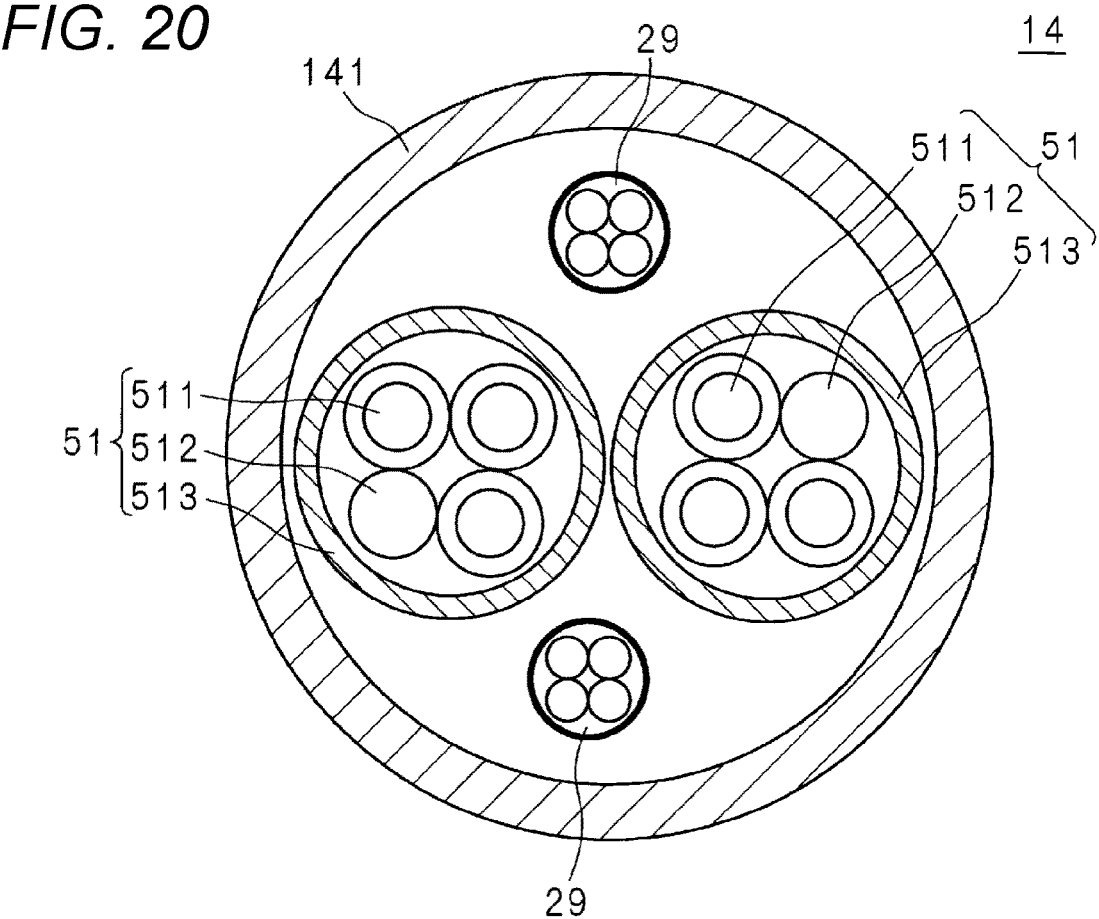
FIG. 20 is a cross-sectional view of the insertion portion according to an eighth embodiment.

FIG. 20 is a cross-sectional view of the insertion portion 14 of the eighth embodiment. FIG. 20 illustrates a cross section similar to that of FIG. 19. In this embodiment, the cable bundle 51 is formed by being divided into two bundles. Each cable bundle 51 contains three cable strands 511 and one reinforcing wire 512, which is covered with the cable sheath 513.

Although not illustrated, the two cable bundles 51 are fixed to the edges of the two opposite sides of the image pickup board 612. The bending mechanism can be realized by winding two cable bundles 51 around the bending shaft 211 instead of the light guide 29 in the sixth embodiment described with reference to FIG. 17.

According to this embodiment, the endoscope 10 having high durability can be provided by using the cable bundle 51 including the reinforcing wire 512 for the bending mechanism.

By arranging two sets of bending knob 21 and bending shaft 211 on the operation unit 20, winding the light guide 29 around one bending shaft 211, and winding the cable bundle 51 around the other bending shaft 211, it is possible to provide the endoscope 10 which is capable of so-called four-way bending.

One cable bundle 51 may be fixed to the edge of the image pickup board 612 as it is. The user can choose whether to tow a single cable bundle 51. It is possible to provide a so-called unidirectionally bending endoscope 10, which can be bent only in one direction.

Ninth Embodiment

This embodiment relates to the endoscope 10 having a bending mechanism using a shape memory alloy wire 174. Descriptions regarding common parts with the sixth embodiment will be omitted.

Figure 21:
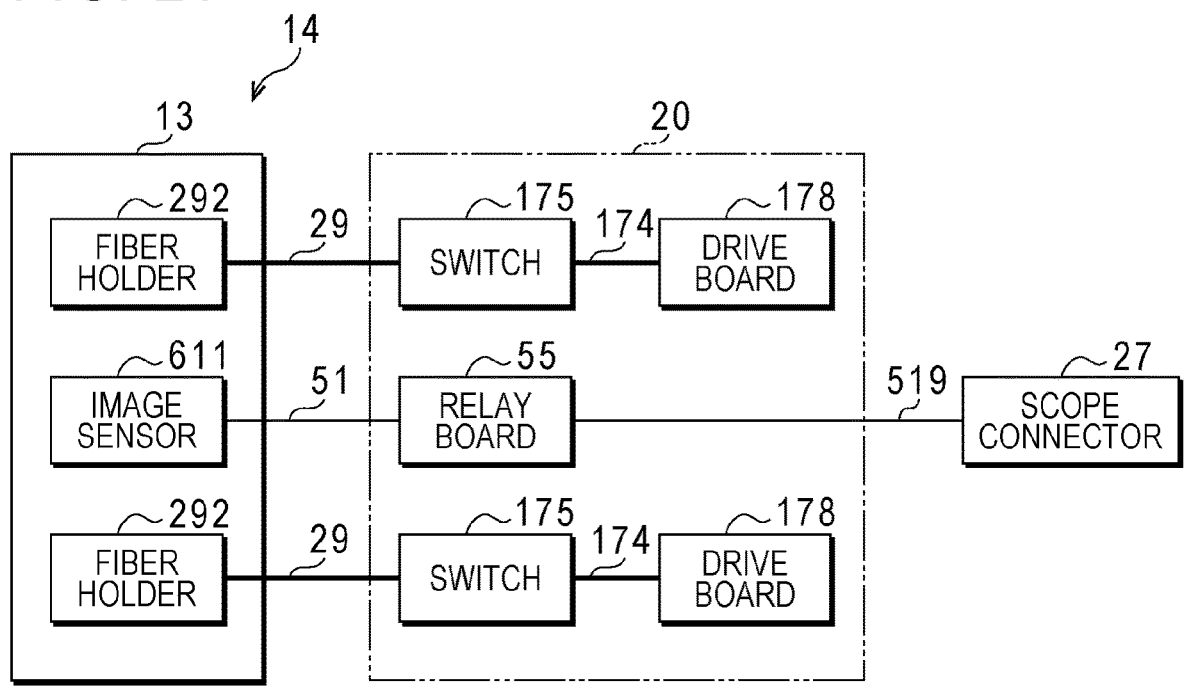
FIG. 21 is an explanatory diagram for explaining a configuration of the operation unit of the endoscope according to a ninth embodiment.

FIG. 21 is an explanatory diagram for explaining the configuration of the operation unit 20 of the endoscope 10 according to the ninth embodiment. In FIG. 21, the configurations of the insertion portion 14 and the operation unit 20 are schematically illustrated, and the branch 18, the second tube 252, and the light guide connector 28 are omitted.

The operation unit 20 is provided with two switches 175. The two switches 175 are configured so that both are not turned on at the same time. Each switch 175 is connected to a drive board 178 via the shape memory alloy wire 174. The drive board 178 is fixed to the operation unit 20. The switch 175 is slidably mounted along the longitudinal direction of the insertion portion 14.

The image sensor 611 is connected to the scope connector 27 via the cable bundle 51, a relay board 55, and a relay cable bundle 519. One end of the light guide fiber 291 bundled with the light guide 29 is fixed to the fiber holder 292. The other end of the light guide 29 is connected to the light guide connector 28, which is not illustrated in FIG. 21. The light guide 29 is fixed to the switch 175 in the middle.

When one of the switches 175 is turned on, the drive board 178 connected to the switch 175 operates to shrink the shape memory alloy wire 174. The switch 175 is pulled by the shape memory alloy wire 174 to slide away from the insertion portion 14.

The shape memory alloy wire 174 and the switch 175 are examples of the traction portion of this embodiment.

The slide of the switch 175 pulls the light guide 29 on the switch 175 side that has been turned on, and the bending section 12 is bent.

According to this embodiment, it is possible to provide the endoscope 10 having a bending function in which the operation unit 20 is miniaturized.

Tenth Embodiment

This embodiment relates to the endoscope 10 having a bending mechanism using a manual tension mechanism. Descriptions regarding common parts with the ninth embodiment will be omitted.

Figure 22:
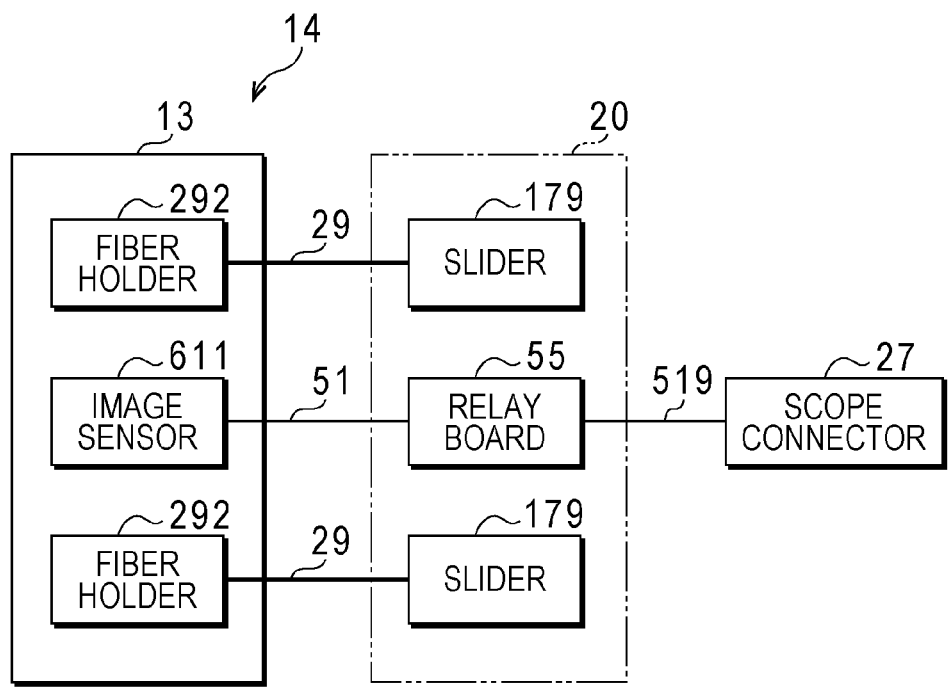
FIG. 22 is an explanatory diagram for explaining a configuration of the operation unit of the endoscope according to a tenth embodiment.

FIG. 22 is an explanatory diagram for explaining the configuration of the operation unit 20 of the endoscope 10 according to the tenth embodiment. In FIG. 22, the configurations of the insertion portion 14 and the operation unit 20 are schematically illustrated, and the branch 18, the second tube 252, and the light guide connector 28 are omitted.

The image sensor 611 is connected to the scope connector 27 via the cable bundle 51, a relay board 55, and a relay cable bundle 519. The operation unit 20 is provided with two sliders 179. One end of the light guide fiber 291 bundled with the light guide 29 is fixed to the fiber holder 292. The other end of the light guide 29 is connected to the light guide connector 28, which is not illustrated in FIG. 22. The light guide 29 is fixed to the slider 179 in the middle.

When the user slides one of the sliders 179, the light guide 29 fixed to the slider 179 is pulled, and the bending section 12 is bent. When the user slides the other slider 179, the bending section 12 is bent in the opposite direction. The slider 179 is an example of the traction portion of this embodiment.

Further, the two sliders 179 may be interlocked so that when one slides, the other one slides in the opposite direction.

According to this embodiment, it is possible to provide the endoscope 10 having a simple structure and a bending function.

Eleventh Embodiment

This embodiment relates to the endoscope 10 having a bending mechanism using a manual tension mechanism. Descriptions regarding common parts with the tenth embodiment will be omitted.

Figure 23A:
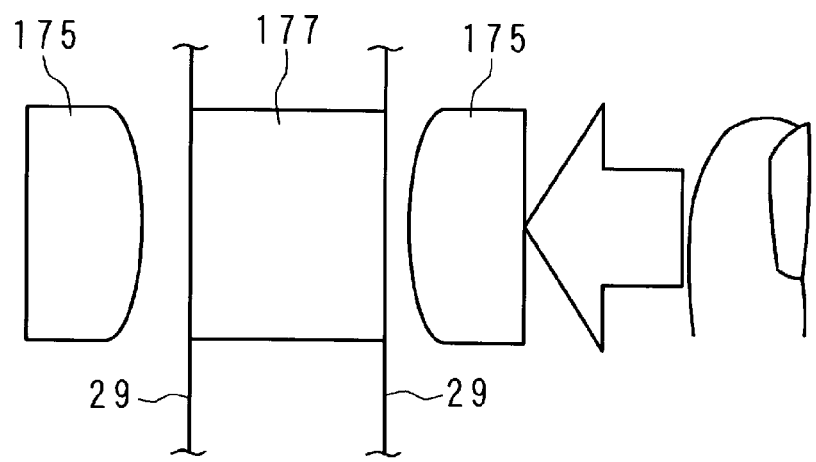
FIG. 23A is an explanatory diagram for explaining the configuration of a tension mechanism according to an eleventh embodiment.
Figure 23B:
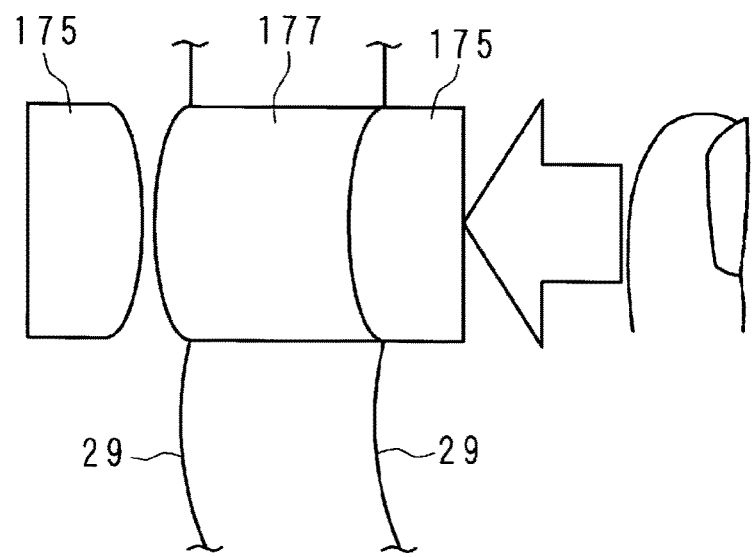
FIG. 23B is an explanatory diagram for explaining the configuration of the tension mechanism according to the eleventh embodiment.

FIGS. 23A and 23B are explanatory diagrams for explaining the configuration of the tension mechanism of the eleventh embodiment. In FIGS. 23A and 23B, the configuration of the tension mechanism provided in the operation unit 20 is schematically illustrated, and the illustration of other parts is omitted.

A block-shaped elastic body 177 is arranged between a set of switches 175. The surface of the switch 175 facing the elastic body 177 is a convex surface. The surface of the elastic body 177 facing the switch 175 is a flat surface.

The light guide 29 is arranged between the switch 175 and the elastic body 177. FIG. 23A illustrates the state before the switch 175 is operated. The switch 175 and the elastic body 177 are separated, and the light guide 29 is in a natural length state.

FIG. 23B illustrates the state after the switch 175 is operated. The switch 175 on the right side in FIG. 23B is pushed by a user's finger to deform the elastic body 177. As the elastic body 177 is deformed, the light guide 29 on the right side bends gently. As a result, the light guide 29 in the insertion portion 14 is pulled.

Since the elastic body 177 is sufficiently flexible, the amount of deformation on the left surface of FIG. 23B is small. Therefore, the other light guide 29 is not pulled. As a result, the bending section 12 is bent to the side corresponding to the light guide 29 on the right side in FIG. 23.

When the user releases the finger from the switch 175, the elastic body 177 returns to its original shape, and the bending section 12 returns to its original shape.

According to this embodiment, it is possible to provide the endoscope 10 having a bending mechanism that automatically returns to its original shape with a simple configuration.

Twelfth Embodiment

This embodiment relates to the endoscope 10 in which an angle holder 293 is fixed to the tip frame 13. Descriptions regarding common parts with the ninth embodiment will be omitted.

Figure 24:
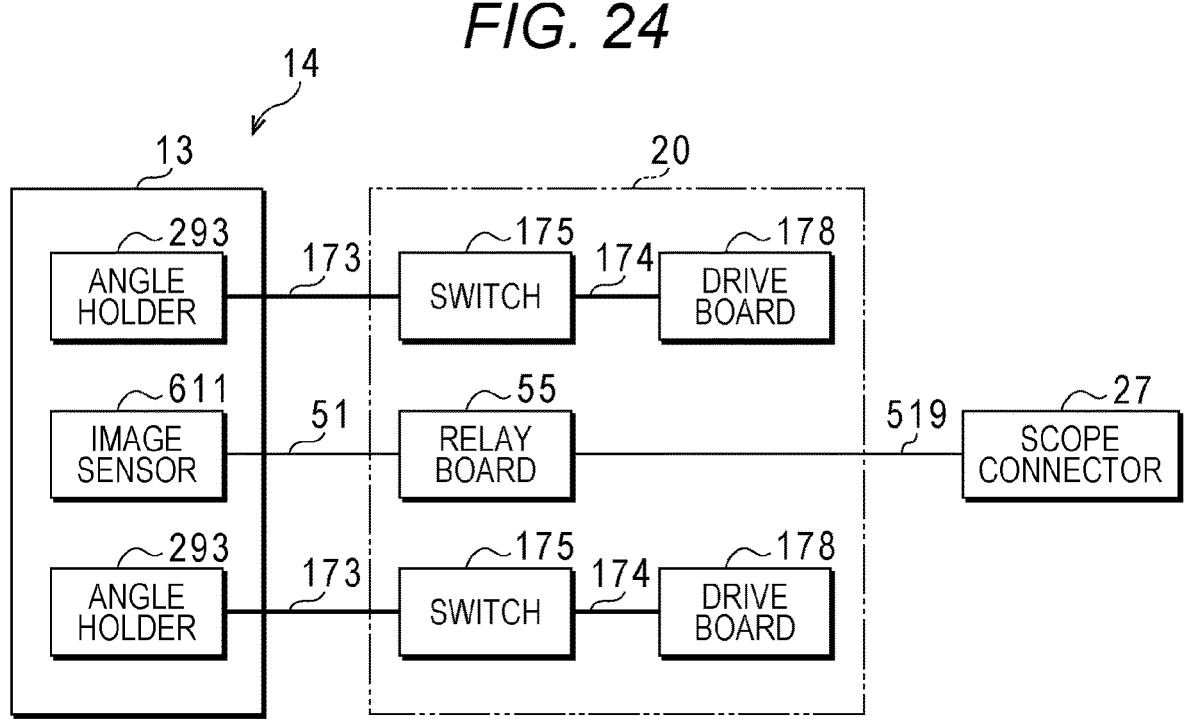
FIG. 24 is an explanatory diagram for explaining the configuration of the tension mechanism according to a twelfth embodiment.

FIG. 24 is an explanatory diagram for explaining the configuration of the tension mechanism of the twelfth embodiment. In FIG. 24, the configurations of the insertion portion 14 and the operation unit 20 are schematically illustrated, and the branch 18, the second tube 252, the light guide connector 28, the fiber holder 292, and the light guide 29 are omitted.

In this embodiment, a tension member 173 is fixed to the switch 175 instead of the light guide 29. The tension member 173 is, for example, a bending wire made of metal. The reinforcing wire 512 included in the cable bundle 51 may be used for the tension member 173.

Figure 25:
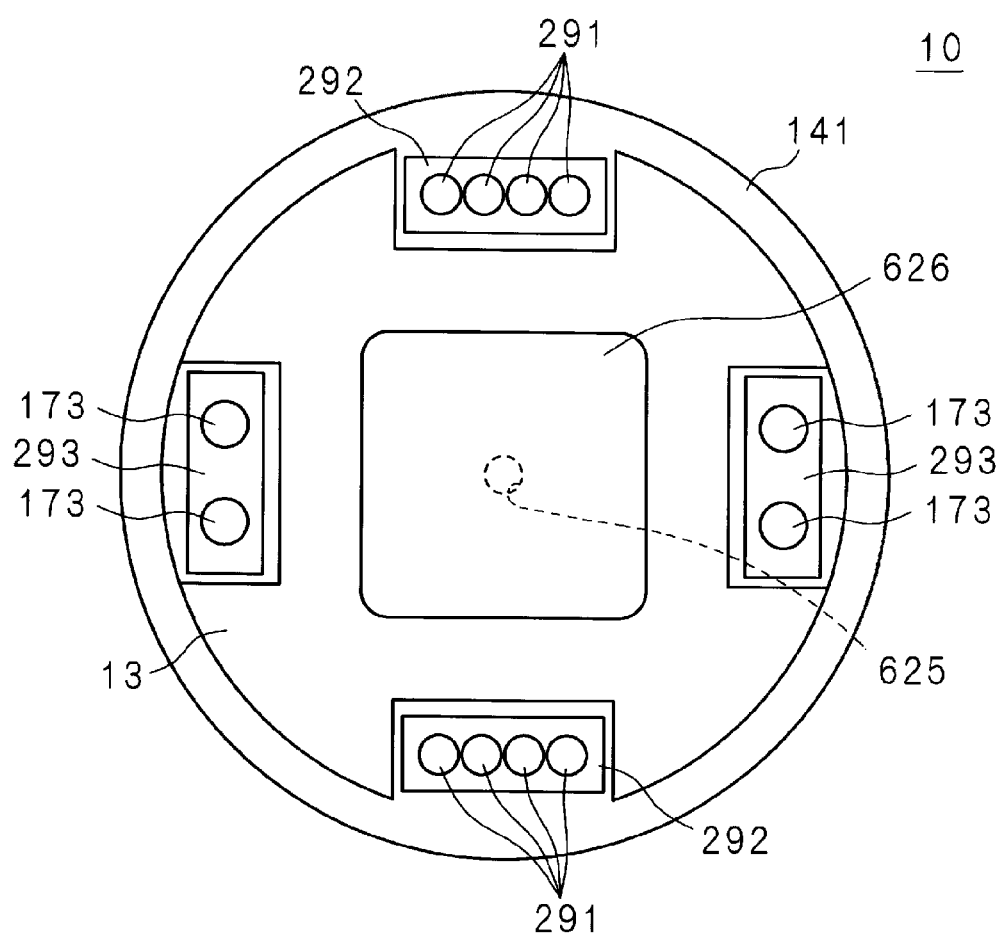
FIG. 25 is an exterior view of the tip of the endoscope according to the twelfth embodiment.

FIG. 25 is an exterior view of the tip of the endoscope 10 according to the twelfth embodiment. In addition to the two fiber holders 292, two angle holders 293 are fixed to the tip frame 13. The fiber holder 292 and the angle holder 293 are alternately and equally arranged along the outer circumference of the tip frame 13. The end portions of the two tension members 173 are fixed to the angle holder 293, respectively.

When one of the switches 175 is turned on, the tension member 173 on the switch 175 side that has been turned on is pulled, and the bending section 12 is bent.

By using the switch 175 that pulls the light guide 29 and the switch 175 that pulls the tension member 173 together as in the ninth embodiment, it is possible to provide the so-called four-way bending endoscope 10 which is capable of being bent in any direction up, down, left, and right.

Thirteenth Embodiment

This embodiment relates to the endoscope 10 having a bending mechanism using a manual tension mechanism. Descriptions regarding common parts with the tenth embodiment will be omitted.

Figure 26:
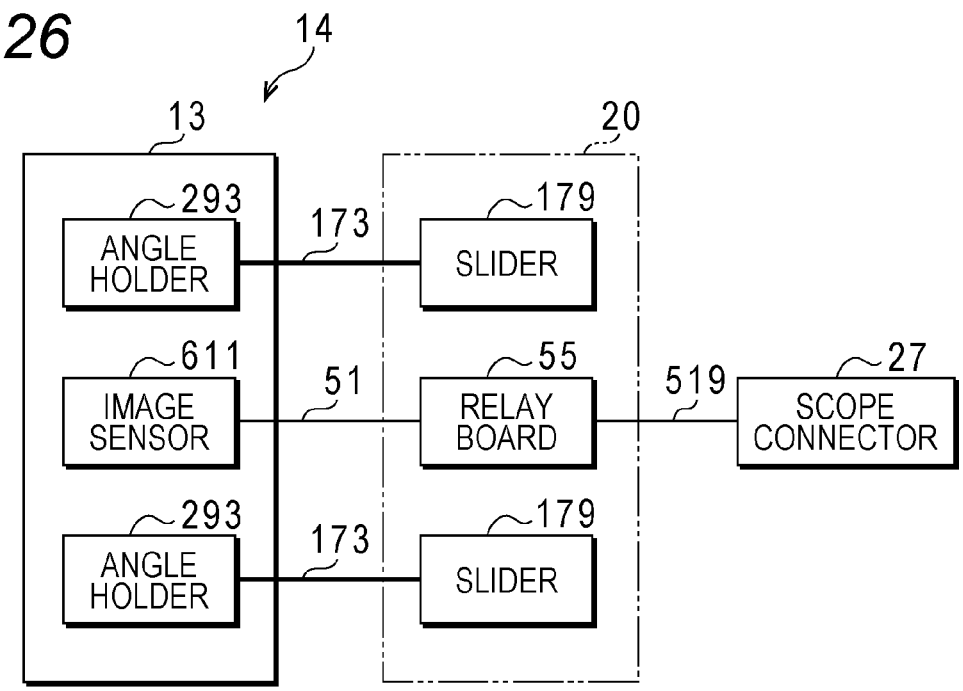
FIG. 26 is an explanatory diagram for explaining the configuration of the tension mechanism according to a thirteenth embodiment.

FIG. 26 is an explanatory diagram for explaining the configuration of the operation unit 20 of the endoscope 10 according to the thirteenth embodiment. In FIG. 26, the configurations of the insertion portion 14 and the operation unit 20 are schematically illustrated, and the branch 18, the second tube 252, the light guide connector 28, the fiber holder 292, and the light guide 29 are omitted.

In this embodiment, the tension member 173 is fixed to the slider 179 instead of the light guide 29. The tension member 173 is, for example, a bending wire made of metal. The reinforcing wire 512 included in the cable bundle 51 may be used for the tension member 173.

The exterior view of the tip of the endoscope 10 of this embodiment is the same as that of FIG. 25. The end portion of the tension member 173 is fixed to the tip frame 13 via the angle holder 293.

When the user slides one of the sliders 179, the tension member 173 fixed to the slid slider 179 is pulled, and the bending section 12 is bent.

According to this embodiment, it is possible to provide the endoscope 10 having a simple structure and a bending function.

Fourteenth Embodiment

This embodiment relates to the endoscope 10 that uses the tension member 173 for bending in each of the four directions. Descriptions regarding common parts with the twelfth embodiment will be omitted.

Figure 27:
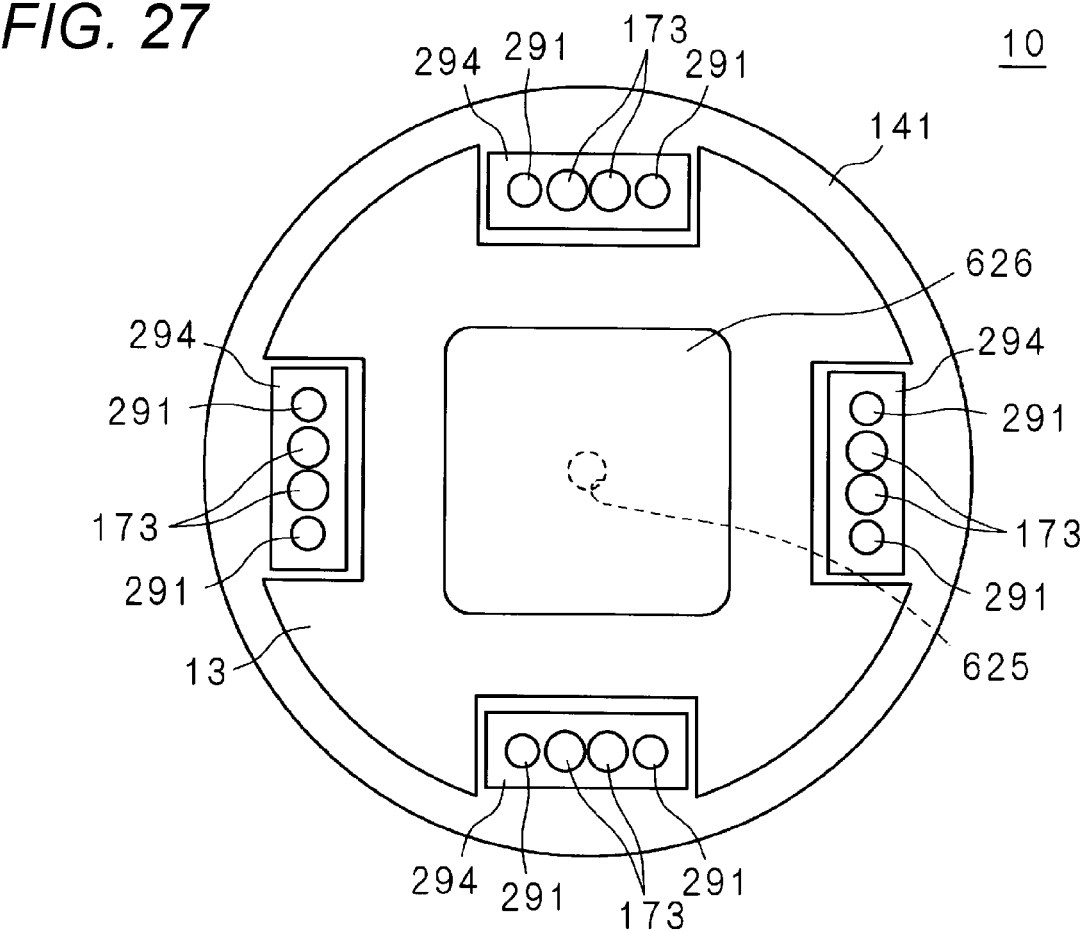
FIG. 27 is an exterior view of the tip of the endoscope according to a fourteenth embodiment.

FIG. 27 is an exterior view of the tip of the endoscope 10 according to the fourteenth embodiment. Four fiber angle holders 294 are fixed to the tip frame 13. The fiber angle holders 294 are evenly arranged on the edge of the tip frame 13.

Two tension members 173 are fixed to each fiber angle holder 294 in the center, and one light guide fiber 291 is fixed to each end. Although not illustrated, four switches 175 are provided in the operation unit, and the tension member 173 is fixed between each switch 175 and the fiber angle holder 294.

When one switch 175 is turned on, the tension member 173 on the switch 175 side that has been turned on is pulled, and the bending section 12 is bent.

According to this embodiment, it is possible to provide the endoscope 10 that does not apply a load due to a tensile force to the light guide fiber 291. Since the end portions of the light guide fibers 291 are distributed around the tip frame 13, it is possible to provide the endoscope 10 that does not generate unnecessary shadows and can obtain a good observation field of view.

Fifteenth Embodiment

This embodiment relates to the endoscope system 30 in which the function of the light source device 34 is built in the endoscope processor 32. Descriptions regarding common parts with the first embodiment will be omitted.

Figure 28:
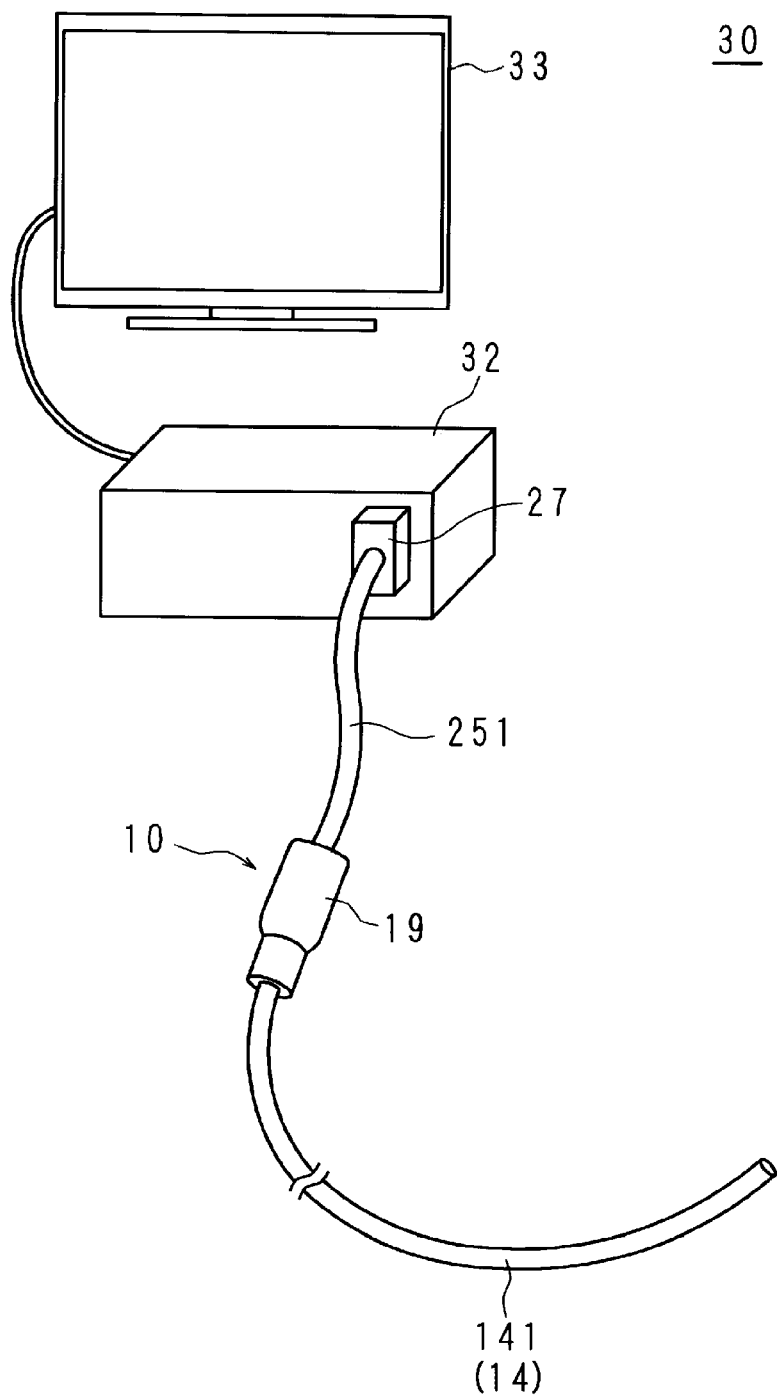
FIG. 28 is an exterior view of the endoscope system according to the fifteenth embodiment.

FIG. 28 is an exterior view of the endoscope system 30 according to the fifteenth embodiment. The endoscope 10 of this embodiment includes the insertion portion 14 covered with the exterior tube 141, a relay portion 19, and the first cord covered with the first tube 251. The insertion portion 14 and the first cord are flexible.

The relay portion 19 has a tubular shape that is thicker than either the exterior tube 141 or the first tube 251. The exterior tube 141 and the first tube 251 communicate with each other via the relay portion 19.

The scope connector 27 connected to the endoscope processor 32 is provided at the end portion of the first tube 251. The scope connector 27 is an example of the connector of this embodiment. The cable bundle 51 and the light guide 29 are connected to the endoscope processor 32 via the exterior tube 141, the relay portion 19, and the first tube 251.

The presence of the relay portion 19 allows the user to grasp the length of the insertion portion 14 inserted into the parent endoscope without taking user's eyes off the display device 33. A connector for connecting the cable strand 511 connected to the image sensor 611 to a thick cable may be provided inside the relay portion 19. By using a thick cable from the middle, attenuation of the video signal can be prevented. Therefore, a good image with less noise can be displayed on the display device 33.

Instead of providing the relay portion 19 and the first tube 251, the scope connector 27 may be provided at the end portion of the exterior tube 141. For example, by making the color of the exterior tube 141 different between the tip side part and the part close to the scope connector 27, or by providing a memory on the surface of the exterior tube 141, the user can grasp the length of the insertion portion 14 inserted into the parent endoscope.

According to this embodiment, since the endoscope processor 32 and the light source device 34 are integrated, it is possible to provide the endoscope system 30 that is easy to install and prepare for endoscopic examination.

Sixteenth Embodiment

This embodiment relates to the endoscope 10 which includes the insertion portion 14 and the operation unit 20. Descriptions regarding common parts with the sixth embodiment will be omitted.

Figure 29:
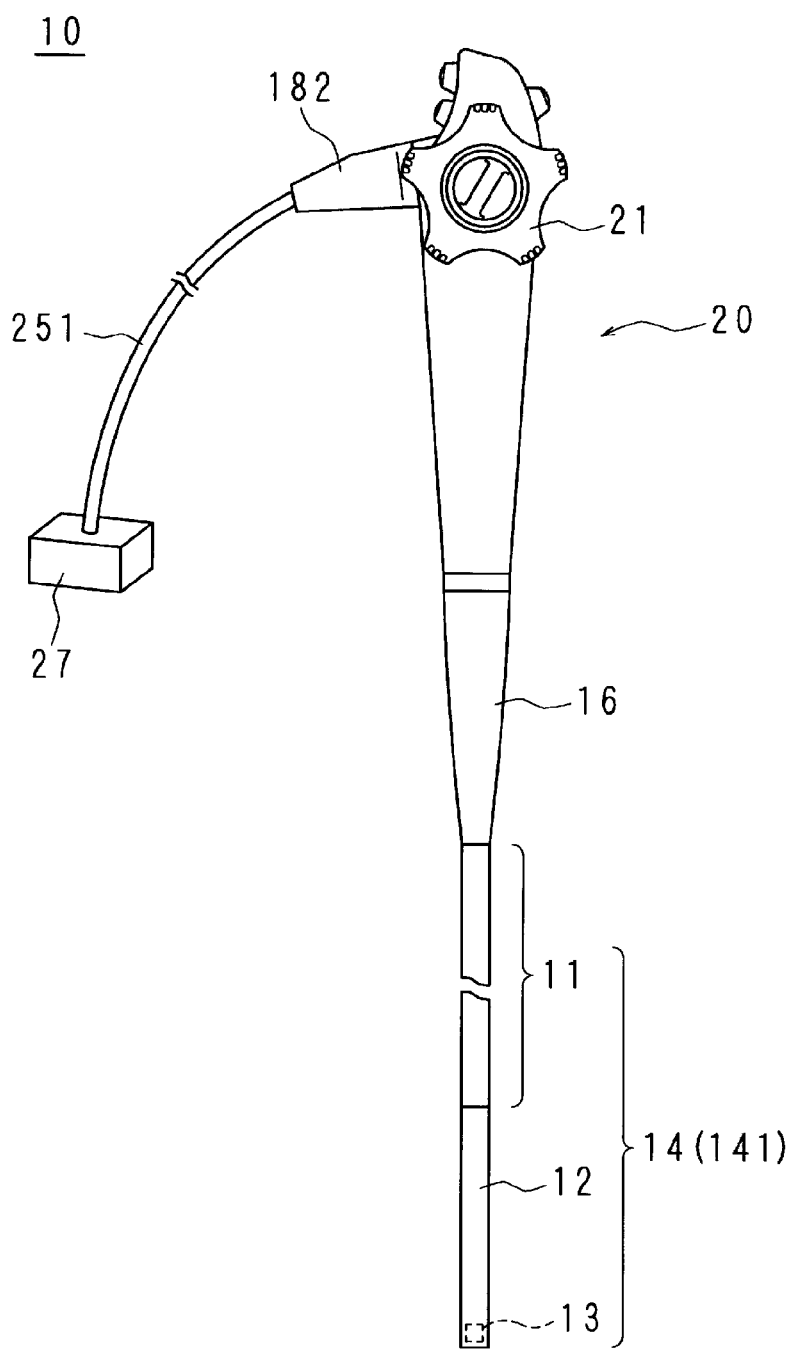
FIG. 29 is an exterior view of the endoscope according to a sixteenth embodiment.

FIG. 29 is an exterior view of the endoscope 10 of the sixteenth embodiment. The endoscope 10 of this embodiment includes the insertion portion 14 and the operation unit 20. The operation unit 20 is provided with the bending knob 21.

The insertion portion 14 is long and has one end connected to the operation unit 20 via a bending preventing portion 16. The insertion portion 14 is covered with the exterior tube 141, and has a soft portion 11, a bending section 12, and the tip frame 13 in this order from the operation unit 20 side. The bending section 12 is bent according to an operation of the bending knob 21.

The first cord covered with the first tube 251 extends from a second bending preventing portion 182 protruding from the operation unit 20. The scope connector 27 is provided at the end portion of the first tube 251.

According to this embodiment, it is possible to provide the endoscope 10 to be used in combination with the endoscope processor 32 having a built-in function of the light source device 34.

Seventeenth Embodiment

This embodiment relates to a comparison of square image sensors 611 of various dimensions. Descriptions regarding common parts with the first embodiment will be omitted.

Figure 30:
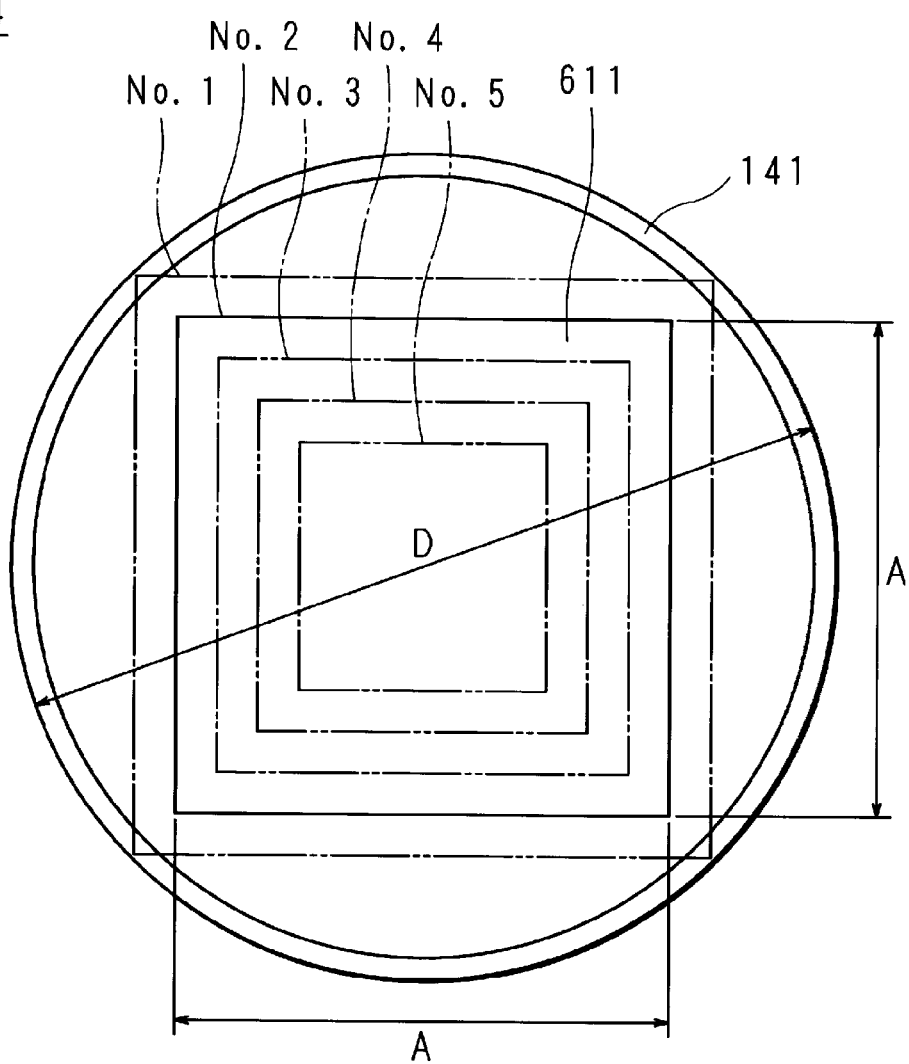
FIG. 30 is a cross-sectional view of an insertion portion taken along an imaging surface of an image sensor according to a seventeenth embodiment.

FIG. 30 illustrates a cross-sectional view of the insertion portion 14 along the imaging surface of the image sensor 611 of the seventeenth embodiment. In FIG. 30, the exterior tube 141 and the image sensor 611 are schematically illustrated by omitting the illustration of the tip frame 13 and the light guide fiber 291.

In FIG. 30, the solid-lined and two-dotted squares indicate the image sensors 611 from No. 1 to No. 5, which have different dimensions. D indicates the outer diameter of the exterior tube 141. A indicates the length of one side of each image sensor 611. In FIG. 30, the dimension line of the length of one side of the No. 2 image sensor 611 illustrated by the solid line is illustrated.

Table 1 illustrates the relationship between the length A of one side of the image sensors 611 of No. 1 to No. 5 and the outer diameter D of the exterior tube 141, and the effectiveness of the image sensor 611 of that dimension.

TABLE 1

| No. | A/D | Effectiveness |
|---|---|---|
| 1 | 0.7 | 3 |
| 2 | 0.6 | 1 |
| 3 | 0.5 | 1 |
| 4 | 0.4 | 2 |
| 5 | 0.3 | 3 |

An effectiveness of "1" means an evaluation that the area of the end surface of the exterior tube 141 is a good size that can be effectively utilized. An effectiveness of "2" means a moderate rating in evaluation. An effectiveness of "3" indicates a low rating in evaluation. For example, in No. 1, the evaluation of effectiveness is low because the image sensor 611 is too large and the exterior tube 141 needs to be made very thin. In No. 5, the evaluation of effectiveness is low because the image sensor 611 is too small to effectively utilize the area of the end surface of the insertion portion 14.

As illustrated in Table 1, it is desirable that the length A of one side of the image sensor 611 is longer than 40% of the outer diameter D of the exterior tube 141 and shorter than 70% of the outer diameter D of the exterior tube 141. It is more desirable that the length A of one side of the image sensor 611 is about 50% to 60% of the outer diameter D of the exterior tube 141.

Figure 31:
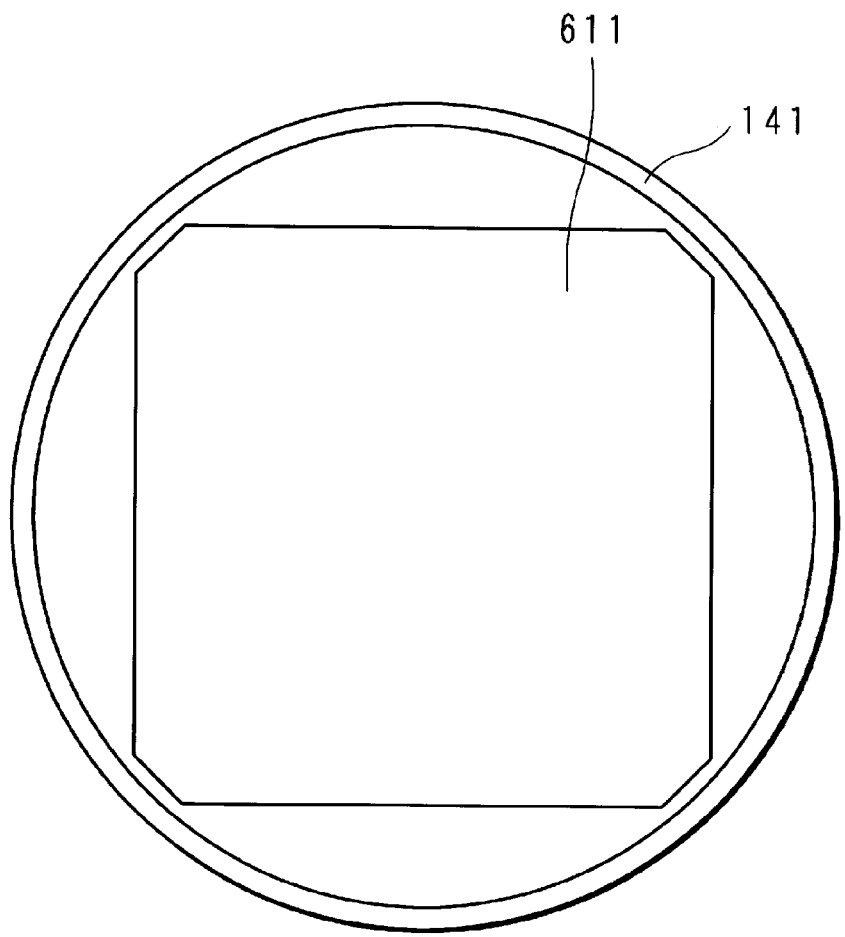
FIG. 31 is a cross-sectional view of an insertion portion taken along an imaging surface of the image sensor of a first modification of the seventeenth embodiment.

FIG. 31 illustrates a cross-sectional view of the insertion portion 14 along the imaging surface of the image sensor 611 of a first modification of the seventeenth embodiment. The image sensor 611 illustrated in FIG. 31 is an octagon with four corners cut off at an angle. By using the image sensor 611 whose corners are cut off diagonally as illustrated in FIG. 31, the effectiveness can be set to 1 even for the image sensor 611 illustrated in No. 1 of Table 1 having a relatively long side.

Figure 32:
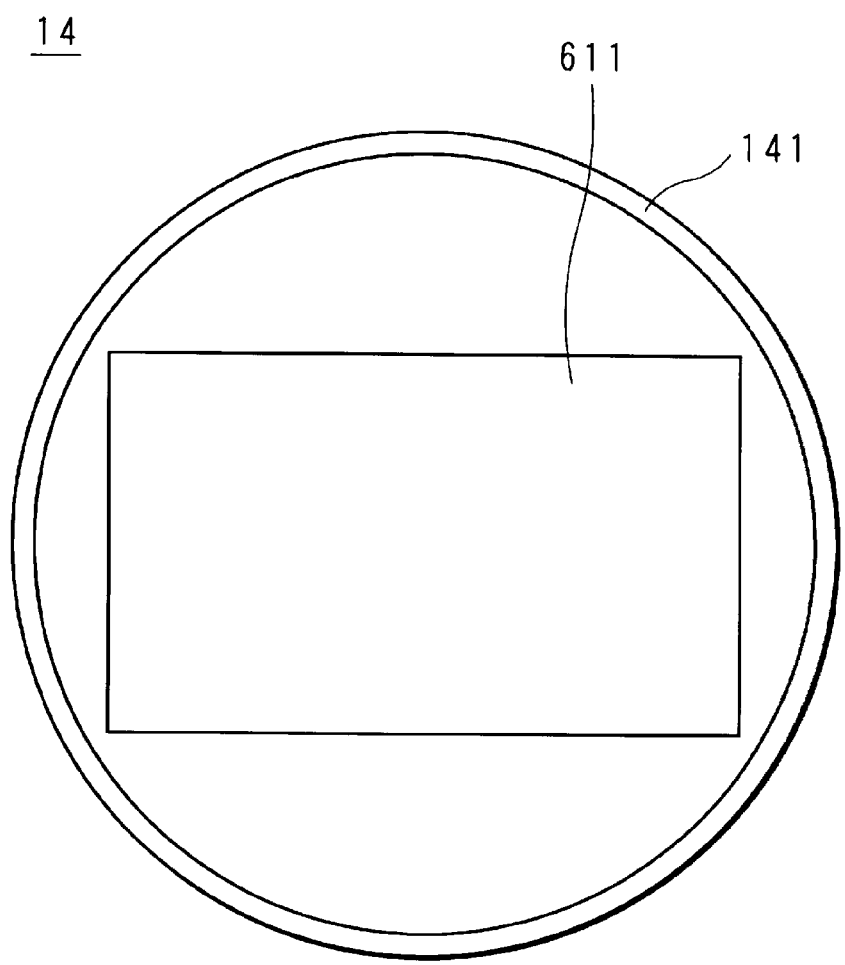
FIG. 32 is a cross-sectional view of an insertion portion taken along the imaging surface of the image sensor of a second modification of the seventeenth embodiment.

FIG. 32 illustrates a cross-sectional view of the insertion portion 14 along the imaging surface of the image sensor 611 of a second modification of the seventeenth embodiment. The image sensor 611 illustrated in FIG. 32 is a rectangle having different vertical and horizontal side lengths. The ratio of the vertical and horizontal sides of the image sensor 611 is arbitrary.

Eighteenth Embodiment

This embodiment relates to a comparison of the covers 626 of various dimensions. Descriptions regarding common parts with the first embodiment will be omitted.

Figure 33:
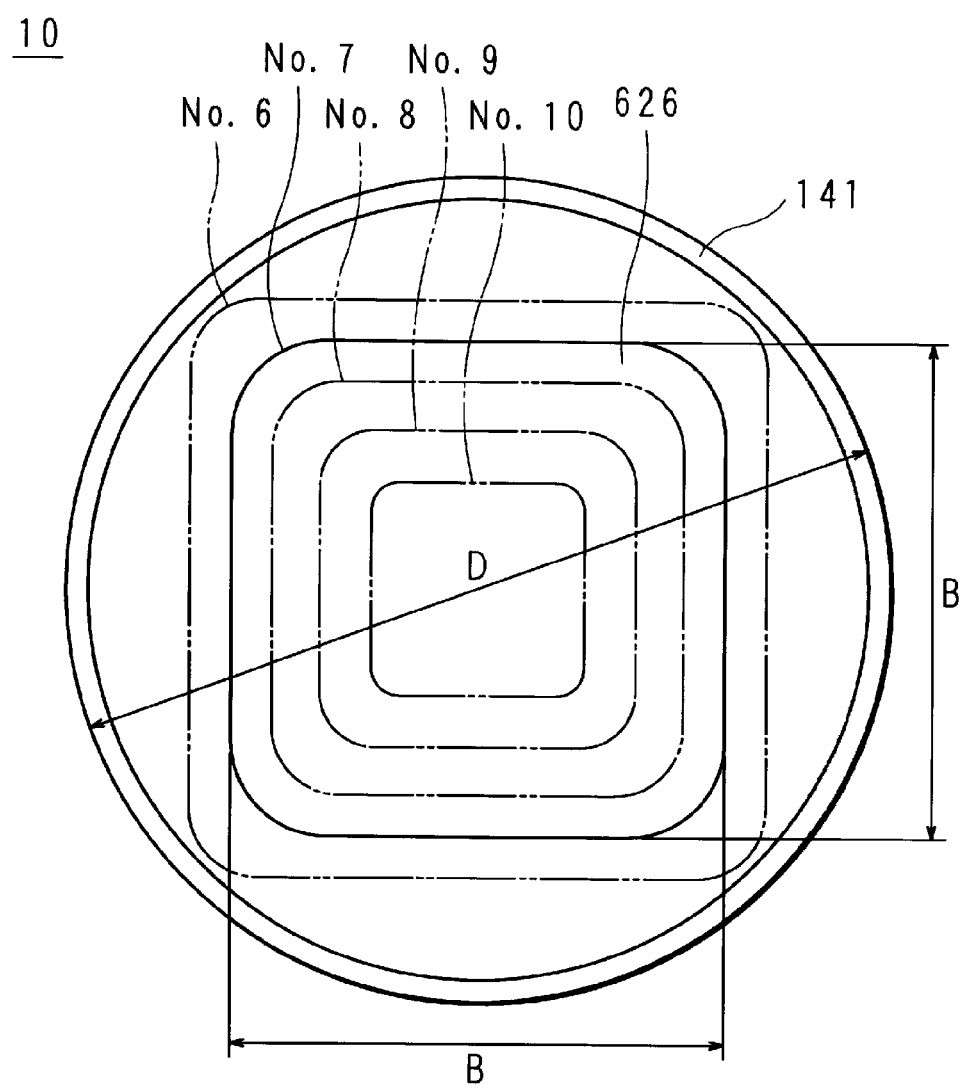
FIG. 33 is an exterior view of the tip of the endoscope according to an eighteenth embodiment.

FIG. 33 is an exterior view of the tip of the endoscope 10 according to the eighteenth embodiment. In FIG. 33, the exterior tube 141 and the cover 626 are schematically illustrated by omitting the illustration of the tip frame 13, the light guide fiber 291, and the fiber holder 292.

In FIG. 33, the solid and two-dotted squares indicate the covers 626 with different dimensions, from No. 6 to No. 10. D indicates the outer diameter of the exterior tube 141. B indicates the length of one side of each cover 626. In FIG. 33, the dimension line of the length of one side of the cover 626 of No. 7 illustrated by the solid line is illustrated.

Table 2 illustrates the relationship between the length B of one side of the covers 626 of No. 6 to No. 10 and the outer diameter D of the exterior tube 141, and the effectiveness of the design using the cover 626. As illustrated in FIG. 3, the image sensor 611 has the dimension equal to that of the cover 626, or smaller than that of the cover 626.

TABLE 2

| No. | B/D | Effectiveness |
|---|---|---|
| 6 | 0.69 | 3 |
| 7 | 0.63 | 1 |
| 8 | 0.5 | 1 |
| 9 | 0.37 | 2 |
| 10 | 0.25 | 3 |

An effectiveness of "1" means an evaluation that the area of the end surface of the exterior tube 141 is a good size that can be effectively utilized. An effectiveness of "2" means a moderate rating in evaluation. An effectiveness of "3" indicates a low rating in evaluation. For example, in No. 6, the cover 626 is too large to secure sufficient space for the light guide fiber 291 and the fiber holder 292, and the evaluation of effectiveness is low. In No. 10, the effectiveness evaluation is low because the cover 626 and the image sensor 611 are too small to effectively utilize the area of the end face of the insertion portion 14.

As illustrated in Table 2, it is desirable that the length B of one side of the cover 626 is longer than 40% of the outer diameter D of the exterior tube 141 and shorter than 70% of the outer diameter D of the exterior tube 141. It is more desirable that the length B of one side of the cover 626 is about 50% to a little over 60% of the outer diameter D of the exterior tube 141.

Technical features (constitutional requirements) described in the respective embodiments can be combined with each other, and new technical features can be formed with the combination.

The embodiments disclosed herein are exemplary in all respects, and it should be considered that the embodiments are not restrictive. The scope of the invention is defined not by the above-described meaning but by claims, and intends to include all modifications within meaning and a scope equal to claims.

REFERENCE SIGNS LIST 10 endoscope
11 soft portion
12 bending section
13 tip frame
134 through hole
135 light guide groove
14 insertion portion
141 exterior tube
1411 first region 1412 second region
16 bending preventing portion
172 bending guide tube
173 tension member
174 shape memory alloy wire
175 switch
177 elastic body
178 drive board
179 slider
18 branch
181 branch portion
182 second bending preventing portion
19 relay portion
20 operation unit
21 bending knob
211 bending shaft
251 first tube
252 second tube
27 scope connector (first connector, connector)
28 light guide connector (second connector)
29 light guide
291 light guide fiber
292 fiber holder
293 angle holder
294 fiber angle holder
30 endoscope system
32 endoscope processor
33 display device
34 light source device
341 first lamp
342 second lamp
343 third lamp
344 fourth lamp
345 fifth lamp
346 sixth lamp
347 seventh lamp
348 light source control unit
35 prism
351 first prism
352 second prism
353 third prism
356 first mirror
357 second mirror
359 condenser lens
51 cable bundle
511 cable strand
512 reinforcing wire
513 cable sheath
519 relay cable bundle
55 relay board
611 image sensor
612 Imaging board
613 spacer
621 imaging lens
624 light-shielding mask
625 mask hole
626 cover

The invention claimed is:

1. An endoscope, comprising:
an insertion portion that is covered with an exterior tube with an outer diameter of 1 mm or less, the insertion portion including a bending section provided on a tip of the insertion portion, and a soft portion which is less bendable than the bending section;
an observation optical system that includes a rectangular image sensor having a rectangular image pickup board and that is fixed to the tip of the insertion portion and having a length of one side of 60% or less of the outer diameter of the insertion portion;
an illumination fiber that is arranged between an inner surface of the exterior tube and an edge of the observation optical system and penetrates the exterior tube;
a cable bundle that is divided into two sub-bundles and is physically and directly connected to the image pickup board and penetrates the exterior tube;
a connector that is connected to the cable bundle and the illumination fiber;
a bending shaft about which the sub-bundles are wound and being capable of towing any one of the sub-bundles between the exterior tube and a first tube by rotation of the bending shaft;
the first tube that is connected to the exterior tube via a branch; and
a second tube that is connected to the exterior tube via the branch,
wherein the connector includes:
a first connector that connects the cable bundle, which is connected to the image sensor to penetrate the exterior tube and the first tube, to an endoscope processor, and
a second connector that connects the illumination fiber, which penetrates the exterior tube and the second tube, to a light source device.

2. The endoscope according to claim 1,
wherein the outer diameter of the insertion portion is 0.5 mm or more.

3. The endoscope according to claim 1,
wherein the length of one side of the image sensor is half of the outer diameter of the insertion portion.

4. The endoscope according to claim 1,
wherein the length of one side of the image sensor is 40% or more of the outer diameter of the insertion portion.

5. The endoscope according to claim 1,
wherein the image sensor is square.

6. The endoscope according to claim 1,
wherein the illumination fiber is arranged between the inner surface of the exterior tube and two non-adjacent sides of the image sensor.

7. The endoscope according to claim 1,
wherein the observation optical system includes
a light-shielding mask that includes a mask hole in the center, and
a lens that is arranged between the light-shielding mask and the image sensor.

8. The endoscope according to claim 7,
wherein the lens is a collimator lens.

9. The endoscope according to claim 1, wherein each sub-bundle includes a reinforcing wire and a plurality of cable strands.

10. An endoscope, comprising:
an insertion portion that is covered with an exterior tube with an outer diameter of 1 mm or less, the insertion portion including a bending section provided on a tip of the insertion portion, and a soft portion which is less bendable than the bending section;
an observation optical system that includes an image sensor having a rectangular image pickup board and that is fixed to the tip of the insertion portion;
an illumination fiber that is arranged between an inner surface of the exterior tube and an edge of the observation optical system;
a pair of cable sub-bundles physically and directly connected to the image pickup board and penetrating the exterior tube; and a bending shaft about which the sub-bundles are wound, the bending shaft being rotatable to tow any one of the sub-bundles for transmitting and receiving a signal to the illumination fiber or the image sensor to bend the insertion portion.

11. The endoscope according to claim 10, wherein each sub-bundle includes a reinforcing wire and a plurality of cable strands.

12. An endoscope system, comprising:
   an endoscope;
   a light source including
      a plurality of light sources that have different emission colors, and
      a light source control unit that controls an emission intensity of the light source; and
   an endoscope processor which generates an image of an object illuminated by the light source,
   wherein the endoscope includes
   an insertion portion that is covered with an exterior tube with an outer diameter of 1 mm or less, the insertion portion including a bending section provided on a tip of the insertion portion, and a soft portion which is less bendable than the bending section,
   an observation optical system that includes a rectangular image sensor having a rectangular image pickup board and that is fixed to the tip of the insertion portion and having a length of one side of 60% or less of the outer diameter of the insertion portion,
   an illumination fiber that is arranged between an inner surface of the exterior tube and an edge of the observation optical system,
   a first tube that is connected to the exterior tube via a branch, and
   a second tube that is connected to the exterior tube via the branch,
   a connector including
      a first connector that connects a cable bundle, which is physically and directly connected to the image pickup board to penetrate the exterior tube and the first tube, and
      a second connector that connects an illumination fiber which penetrates the exterior tube and the second tube, to the light source, wherein
      the cable bundle is divided into two sub-bundles, and
      the endoscope includes a bending shaft about which the sub-bundles are wound and being capable of towing any one of the sub-bundles between the exterior tube and the first tube.

13. The endoscope system according to claim 12, wherein each sub-bundle includes a reinforcing wire and a plurality of cable strands.

* * * * *